US012635934B2

(12) United States Patent
Kwon et al.

(10) Patent No.: US 12,635,934 B2
(45) Date of Patent: May 26, 2026

(54) SYSTEMS, DEVICES AND METHODS RELATED TO PERIODONTAL MEASUREMENTS

(71) Applicants: Paul Kwon, Quincy, WA (US); Stephanie Kwon, Quincy, WA (US)

(72) Inventors: Paul Kwon, Quincy, WA (US); Stephanie Kwon, Quincy, WA (US)

( * ) Notice: Subject to any disclaimer, the term of this patent is extended or adjusted under 35 U.S.C. 154(b) by 147 days.

(21) Appl. No.: 18/666,848

(22) Filed: May 17, 2024

(65) Prior Publication Data

US 2024/0298962 A1    Sep. 12, 2024

Related U.S. Application Data

(63) Continuation of application No. PCT/US2022/050965, filed on Nov. 23, 2022.

(Continued)

(51) Int. Cl.
*A61B 6/14* (2006.01)
*A61B 5/00* (2006.01)
(Continued)

(52) U.S. Cl.
CPC .......... *A61B 5/4552* (2013.01); *A61B 5/0088* (2013.01); *A61B 5/4547* (2013.01);
(Continued)

(58) Field of Classification Search
CPC ....... A61B 5/4552; A61B 6/51; A61B 5/0088; A61B 5/4547; A61B 6/032; A61B 6/4085;
(Continued)

(56) References Cited

U.S. PATENT DOCUMENTS

2014/0234796 A1* 8/2014 Tsuji ..................... A61B 6/032
433/29
2016/0310097 A1* 10/2016 Bae .......................... A61B 6/51
(Continued)

FOREIGN PATENT DOCUMENTS

EP          2452652 A1       5/2012
KR      10-1536543 B1       7/2015

OTHER PUBLICATIONS

International Search Report dated Apr. 17, 2023 for PCT/US2022/050965.

(Continued)

*Primary Examiner* — Abdul-Samad A Adediran
(74) *Attorney, Agent, or Firm* — Chang & Hale LLP

(57)          ABSTRACT

In some embodiments, a method for measuring a periodontal condition can include generating or obtaining radiograph data for a tooth and a respective bone structure, generating or obtaining surface data for the tooth, the surface data including surface information of a gum tissue associated with the tooth, and combining the radiograph data and the surface data such that a feature of the tooth in the radiograph data substantially matches with a corresponding feature of the tooth in the surface data. The method can further include calculating a periodontal parameter from the combination of the radiograph data and the surface data, with the periodontal parameter being indicative of the periodontal condition.

20 Claims, 33 Drawing Sheets

Related U.S. Application Data

(60) Provisional application No. 63/352,951, filed on Jun. 16, 2022, provisional application No. 63/282,789, filed on Nov. 24, 2021.

(51) Int. Cl.
| | |
|---|---|
| *A61B 6/00* | (2006.01) |
| *A61B 6/03* | (2006.01) |
| *A61B 6/40* | (2024.01) |
| *A61B 6/51* | (2024.01) |
| *G06T 7/00* | (2017.01) |

(52) U.S. Cl.
CPC ............ *A61B 6/032* (2013.01); *A61B 6/4085* (2013.01); *A61B 6/51* (2024.01); *A61B 6/5247* (2013.01); *G06T 7/0012* (2013.01); *G06T 2207/10081* (2013.01); *G06T 2207/30036* (2013.01)

(58) Field of Classification Search
CPC ....... A61B 6/5247; A61B 1/24; G06T 7/0012; G06T 2207/10081; G06T 2207/30036

USPC .......................................................... 433/29
See application file for complete search history.

(56) References Cited

U.S. PATENT DOCUMENTS

| | | | |
|---|---|---|---|
| 2018/0078347 A1* | 3/2018 | Falkel | ...................... A61B 1/24 |
| 2020/0000568 A1 | 1/2020 | Shindo | |
| 2020/0364860 A1 | 11/2020 | Kearney et al. | |

OTHER PUBLICATIONS

Written Opinion dated Apr. 17, 2023 for PCT/US2022/050965.
Chung, H.-M. et al., "Periodontal Measurement on Digital Images Reveals Risk of Overestimation in Clinical Periodontal Probing in Periodontitis Patients", Research Square, Jun. 30, 2021, pp. 1-11, Preprint version <DOI: https://doi.org/10.21203/rs.3.rs-654031/v1>.
Wang, L. et al., "Accuracy of assessing gingival thickness in the esthetic maxillary region by periodontal probing, cone-beam computed tomography and digital scanning", Int. J. Clin. Exp. Med., 2019, vol. 12, No. 8, pp. 10302-10309.

* cited by examiner

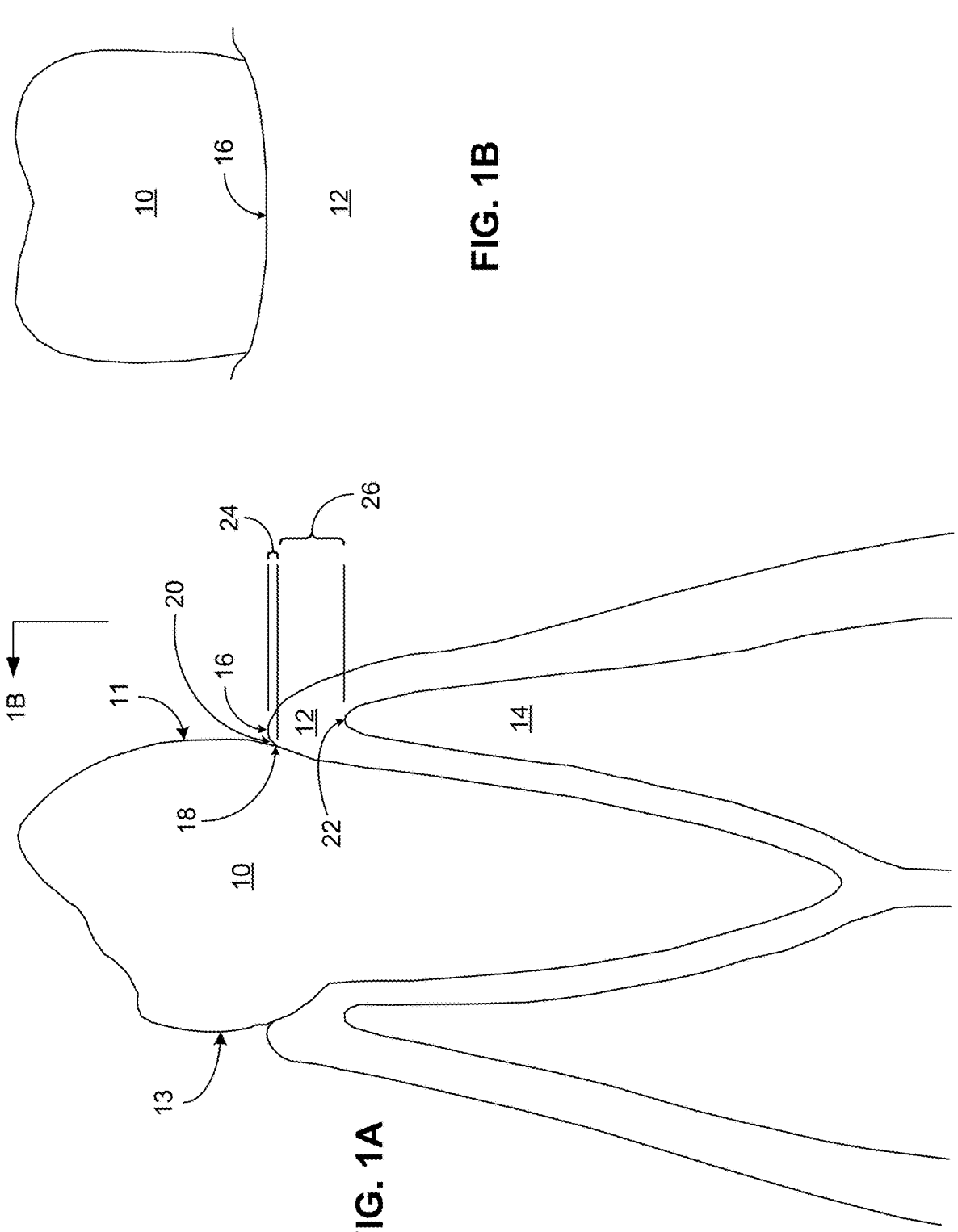

210

212

Obtain CBCT radiograph of teeth and associated bone structures

214

Obtain a scan of the teeth and associated gum lines

216

Combine the CBCT radiograph and the scan to determine relative positions of the gum lines and the respective bone structures

218

Estimate gum pocket depths based on the relative positions of the gum lines and the bone structures

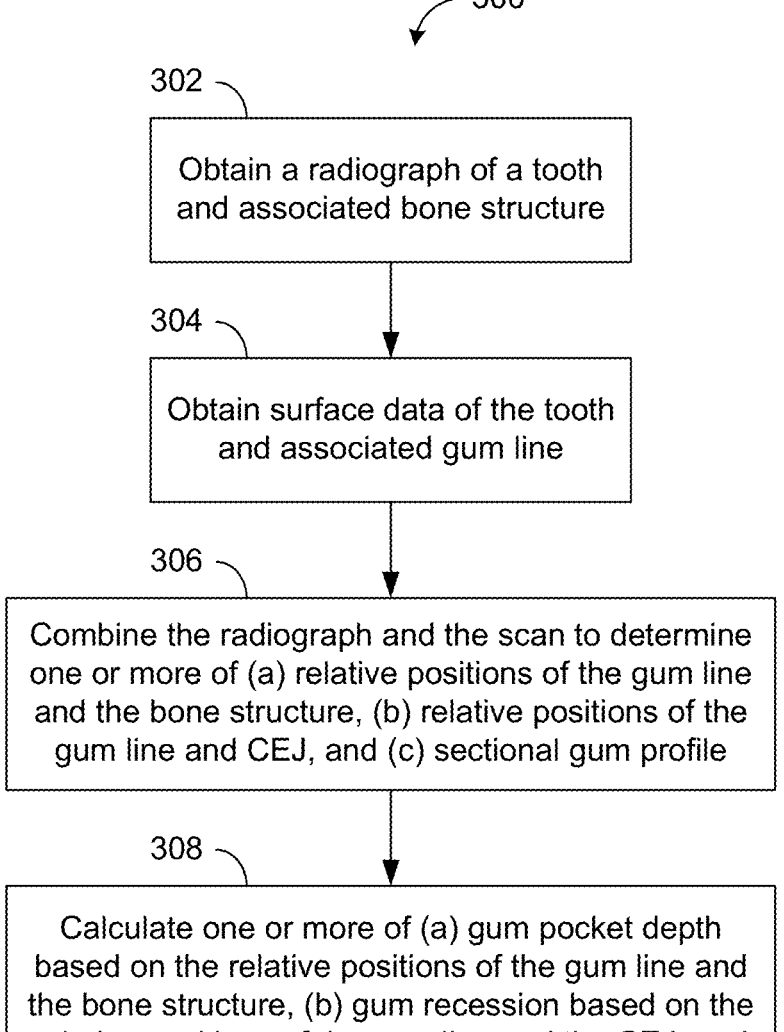

300

302

Obtain a radiograph of a tooth and associated bone structure

304

Obtain surface data of the tooth and associated gum line

306

Combine the radiograph and the scan to determine one or more of (a) relative positions of the gum line and the bone structure, (b) relative positions of the gum line and CEJ, and (c) sectional gum profile

308

Calculate one or more of (a) gum pocket depth based on the relative positions of the gum line and the bone structure, (b) gum recession based on the relative positions of the gum line and the CEJ, and (c) gum thickness based on the sectional gum profile

FIG. 16A

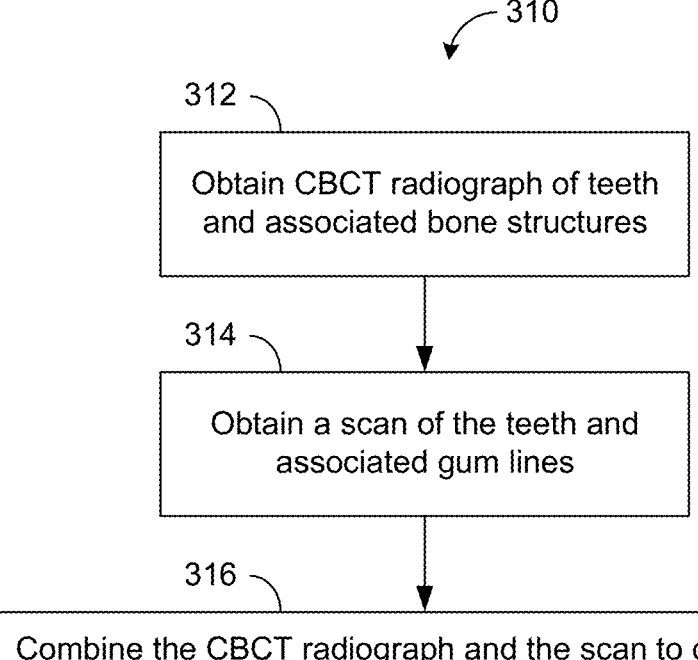

310

312

Obtain CBCT radiograph of teeth
and associated bone structures

314

Obtain a scan of the teeth and
associated gum lines

316

Combine the CBCT radiograph and the scan to determine
some or all of (a) relative positions of the gum lines and the
bone structures, (b) relative positions of the gum lines and
CEJs, and (c) sectional gum profiles

318

Calculate some or all of (a) gum pocket depths based on
the relative positions of the gum lines and the bone
structures, (b) gum recessions based on the relative
positions of the gum lines and the CEJs, and (c) gum
thicknesses based on the sectional gum profiles

Calculate some or all of (a) gum pocket depth, (b) gum recession, and (c) gum thickness, at one or more locations for each of a set of teeth

324

Generate an output with information representative of gum condition for the set of teeth based on the estimated gum pocket depths, gum recessions, and/or gum thicknesses

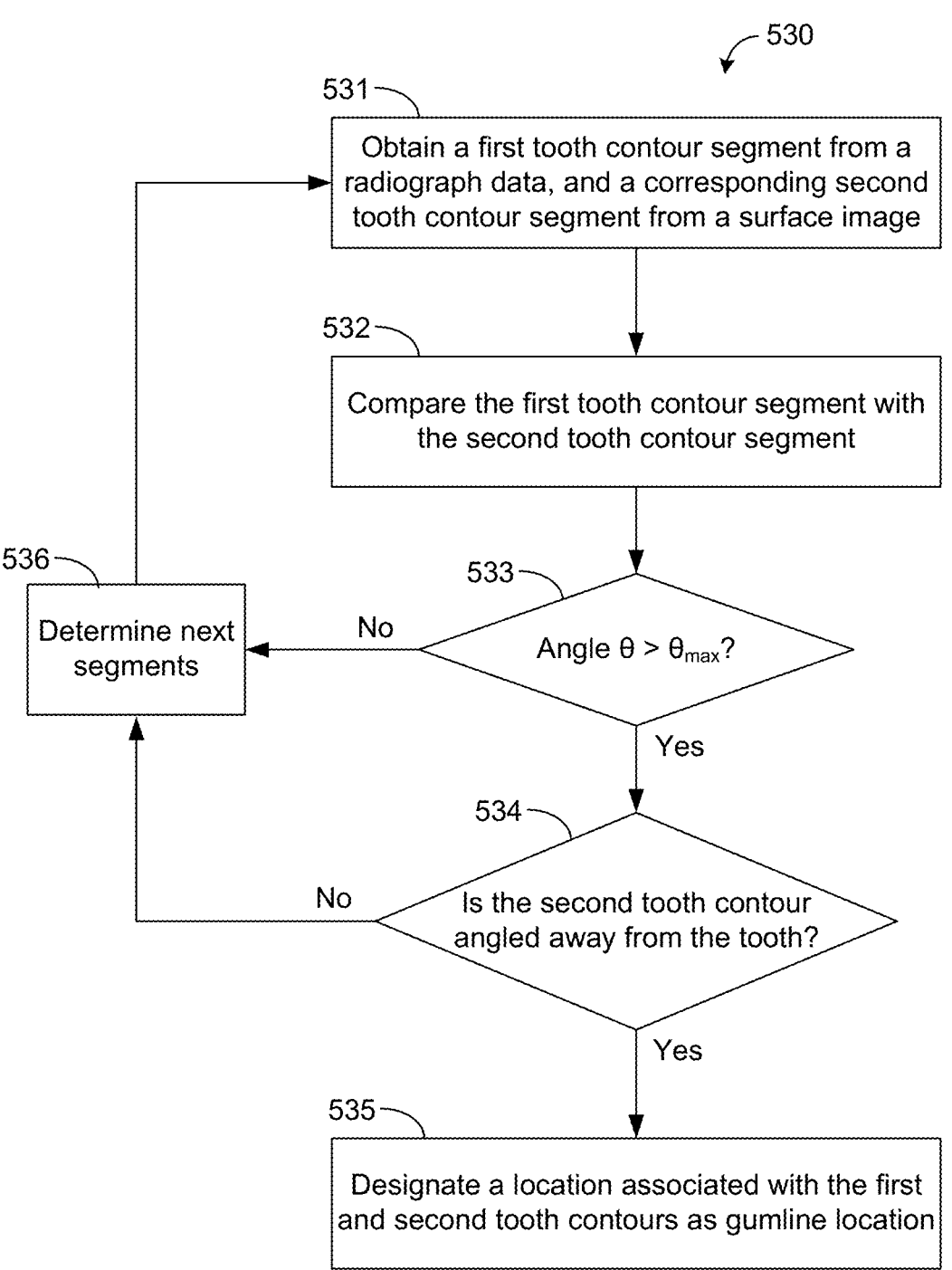

531 — Obtain a first tooth contour segment from a radiograph data, and a corresponding second tooth contour segment from a surface image 532 — Compare the first tooth contour segment with the second tooth contour segment 533 — Angle θ > θ$_{max}$?

No → 536 — Determine next segments

Yes

534 — Is the second tooth contour angled away from the tooth?

No

Yes

535 — Designate a location associated with the first and second tooth contours as gumline location

SYSTEMS, DEVICES AND METHODS RELATED TO PERIODONTAL MEASUREMENTS

CROSS-REFERENCE TO RELATED APPLICATION(S)

This application is a continuation of International Application No. PCT/US2022/050965 filed Nov. 23, 2022, entitled SYSTEMS, DEVICES AND METHODS RELATED TO PERIODONTAL MEASUREMENTS, which claims priority to U.S. Provisional Application Nos. 63/282,789 filed Nov. 24, 2021, entitled SYSTEMS, DEVICES AND METHODS RELATED TO PERIODONTAL MEASUREMENTS, and 63/352,951 filed Jun. 16, 2022, entitled SYSTEMS, DEVICES AND METHODS RELATED TO PERIODONTAL MEASUREMENTS, the disclosure of each of which is hereby expressly incorporated by reference herein in its entirety.

BACKGROUND

Field

The present disclosure relates to systems, devices and methods related to periodontal measurements.

Description of the Related Art

Periodontal disease typically involves infection and inflammation of gum and bone associated with a given tooth. When in a more advanced form, such a periodontal disease can include the gum separating from the tooth and/or loss of bone supporting the tooth.

In some dental applications, periodontal disease can be detected and/or characterized by, for example, measurement of depth of a pocket formed between a given tooth and the gum separating from the tooth. Such a pocket-depth measurement is typically achieved utilizing a mechanical probe device.

SUMMARY

In some implementations, the present disclosure relates to a method for measuring a periodontal condition. The method includes generating or obtaining radiograph data for a tooth and a respective bone structure, and generating or obtaining surface data for the tooth, with the surface data including surface information of a gum tissue associated with the tooth. The method further includes combining the radiograph data and the surface data such that a feature of the tooth in the radiograph data substantially matches with a corresponding feature of the tooth in the surface data. The method further includes calculating a periodontal parameter from the combination of the radiograph data and the surface data, with the periodontal parameter being indicative of the periodontal condition.

In some embodiments, the radiograph data can include computed tomography (CT) radiograph data such as cone beam computed tomography (CBCT) radiograph data. The scan data can include scan data such as intraoral scan data.

In some embodiments, the calculating of the periodontal parameter can include calculating a dimension indicative of the periodontal condition. The calculating of the dimension can include generating a merged data plane that extends through the tooth and includes a gumline location on a selected side of the tooth. The merged data plane can further include another gumline location. The gumline location and the other gumline location can be on opposing sides of the tooth.

In some embodiments, the merged data plane can form an angle with respect to a tangent line at the gumline location, and the angle can have a value in a range of 60 degrees to 120 degrees, 70 degrees to 110 degrees, 80 degrees to 100 degrees, or 85 degrees to 95 degrees.

In some embodiments, the calculating of the dimension can further include determining a distance between the gumline location and a bone location. The determining of the distance can include identifying the gumline location and the bone location.

In some embodiments, each of either or both of the gumline location and the bone location can be identified with one or more algorithms having some or all of artificial intelligence, machine learning and neural network functionalities.

In some embodiments, the gumline location can be identified based on an intersection of a first segment representative of the matched feature of the tooth and a second segment representative of a feature of the gum tissue. The second segment can extend away from the tooth at an angle. The bone location can be calculated based on an intersection of a third segment representative of a feature of the tooth and a fourth segment representative of a feature of the bone structure. The fourth segment can extend away from the tooth at an angle.

In some embodiments, the calculating of the dimension can further include subtracting a value from the distance between the gumline location and the bone location. In some embodiments, the value can include a biologic width value.

In some embodiments, the method can further include characterizing another periodontal parameter from the radiograph data, the surface data or the combination of radiograph and surface data, with the other periodontal parameter providing additional information about the periodontal condition. The periodontal parameter can include one of a gum pocket depth dimension, a gum recession dimension and a clinical attachment level dimension. In some embodiments, the other periodontal parameter can be another one of the gum pocket depth dimension, the gum recession dimension and the clinical attachment level dimension. In some embodiments, the other periodontal parameter can include an alveolar crest height dimension, a gumline profile, a measure of gum inflammation or a measure or presence of abfraction.

In some implementations, the present disclosure relates to a system for measuring a periodontal condition. The system is configured to combine radiograph data for a tooth and a respective bone structure and surface data for the tooth and a respective gum tissue. The system is further configured to calculate a periodontal parameter from the combined data, with the periodontal parameter being indicative of the periodontal condition.

In some embodiments, the periodontal parameter can include a dimension indicative of the periodontal condition.

In some embodiments, the radiograph data can include cone beam computed tomography (CBCT) radiograph data, and the surface data can include intraoral scan data.

In some embodiments, the system can include a CBCT apparatus for generating the CBCT radiograph data, and an intraoral scanner for generating the intraoral scan data.

In some embodiments, the system can include a CBCT apparatus for generating the CBCT radiograph data, and the intraoral scan data can be obtained from an external intraoral scanner that is not part of the system.

In some embodiments, the system can include an intraoral scanner for generating the intraoral scan data, and the CBCT radiograph data can be obtained from an external CBCT apparatus that is not part of the system.

In some embodiments, the CBCT radiograph data can be obtained from an external CBCT apparatus that is not part of the system, and the intraoral scan data can be obtained from an external intraoral scanner that is not part of the system.

In some implementations, the present disclosure relates to a non-transitory computer readable medium having stored thereon software instructions that, when executed by a processor, cause the processor to interpret a data stream, by executing steps that include accessing radiograph data for a tooth and a respective bone structure, accessing surface data for the tooth, with the surface data including surface information of a gum tissue associated with the tooth, combining the radiograph data and the surface data such that a feature of the tooth in the radiograph data substantially matches with a corresponding feature of the tooth in the surface data, and calculating a periodontal parameter from the combination of the radiograph data and the surface data, with the periodontal parameter being indicative of the periodontal condition.

In some implementations, the present disclosure relates to a method for measuring condition of gum tissue. The method includes generating or obtaining radiograph data for one or more teeth and respective bone structures, generating or obtaining surface data for the one or more teeth, with the surface data including surface information of a gum tissue associated with each of the one or more teeth, and combining the radiograph data and the surface data such that the one or more teeth in the radiograph data substantially matches with the one or more teeth in the surface data. The method further includes calculating a dimension of a portion of the gum tissue associated with each of the one or more teeth based on the combination of the radiograph data and the surface data.

In some embodiments, the radiograph data can include computed tomography (CT) radiograph data such as cone beam computed tomography (CBCT) radiograph data. The surface data can include scan data such as intraoral scan data.

In some embodiments, the method can further include providing or obtaining a biologic width value associated with each of the one or more teeth. The calculating of the dimension can include calculating a depth dimension of a pocket formed between each tooth and the respective gum tissue based on the combination of the radiograph data and the surface data. The calculating of the depth dimension can include identifying a gumline and a top portion of the bone structure for each tooth in the combination of the radiograph data and the surface data. The depth dimension of the pocket can include a distance between the gumline and the top portion of the bone structure, minus the biologic width value. The calculating of the depth dimension of the pocket can be performed for a plurality of locations for each tooth. The plurality of locations for each tooth can include some or all of buccal distal, buccal mid, buccal mesial, lingual distal, lingual mid and lingula mesial locations of the tooth.

In some embodiments, the biologic width value can be a constant value for each of the one or more teeth. Such a constant value can be, for example, approximately 2 mm.

In some embodiments, the method can further include generating an output representative of the calculated dimension. The output can include display data configured to provide a visual representation of a gum tissue condition. The output can include values formatted to be included in a patient record.

In some embodiments, the dimension can include a gum pocket depth, a gum recession value, a clinical attachment level value, or a gum thickness value.

In some implementations, the present disclosure relates to a system for measuring condition of gum tissue. The system is configured to combine radiograph data and surface data for one or more teeth such that the one or more teeth in the radiograph data substantially matches with the one or more teeth in the surface data. The system is further configured to calculate one or more dimensions of a gum tissue associated with each of the one or more teeth based on the combination of the radiograph data and the surface data.

In some embodiments, the radiograph data can include cone beam computed tomography (CBCT) radiograph data, and the surface data can include intraoral scan data.

In some embodiments, the system can include a CBCT apparatus for generating the CBCT radiograph data, and an intraoral scanner for generating the intraoral scan data.

In some embodiments, the system can include a CBCT apparatus for generating the CBCT radiograph data, and the intraoral scan data can be obtained from an external intraoral scanner that is not part of the system.

In some embodiments, the system includes an intraoral scanner for generating the intraoral scan data, and the CBCT radiograph data can be obtained from an external CBCT apparatus that is not part of the system.

In some embodiments, the CBCT radiograph data can be obtained from an external CBCT apparatus that is not part of the system, and the intraoral scan data can be obtained from an external intraoral scanner that is not part of the system.

In some embodiments, the one or more teeth can include an entire set of teeth of a patient.

In some embodiments, the one or more dimensions can include one or more of a gum pocket depth, a gum recession value, a clinical attachment level value, and a gum thickness value.

In some embodiments, the system can be further configured to generate an output representative of the one or more dimensions. Such an output can be configured to be included in a patient record.

In some implementations, the present disclosure relates to a non-transitory computer readable medium having stored thereon software instructions that, when executed by a processor, cause the processor to interpret a data stream, by executing steps that include accessing radiograph data for one or more teeth and respective bone structures, accessing surface data for the one or more teeth, with the surface data including surface information of a gum tissue associated with each of the one or more teeth, combining the radiograph data and the surface data such that the one or more teeth in the radiograph data substantially matches with the one or more teeth in the surface data, and calculating one or more dimensions of a gum tissue associated with each of the one or more teeth based on the combination of the radiograph data and the surface data.

For purposes of summarizing the disclosure, certain aspects, advantages and novel features of the inventions have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

FIG. 1A shows a side sectional view of a tooth having a healthy gum tissue.

FIG. 1B shows a front view of the tooth of FIG. 1A.

FIG. 16A shows a process that can be implemented by a system having one or more features as described herein.

FIG. 16B shows a process that can be a more specific example of the process of FIG. 16A.

FIG. 26 shows a process that can be implemented to calculate a gumline location in a merged data plane, such as the example merged data plane of FIG. 25.

DETAILED DESCRIPTION OF SOME EMBODIMENTS

The headings provided herein, if any, are for convenience only and do not necessarily affect the scope or meaning of the claimed invention.

Figures 2A, 2B:
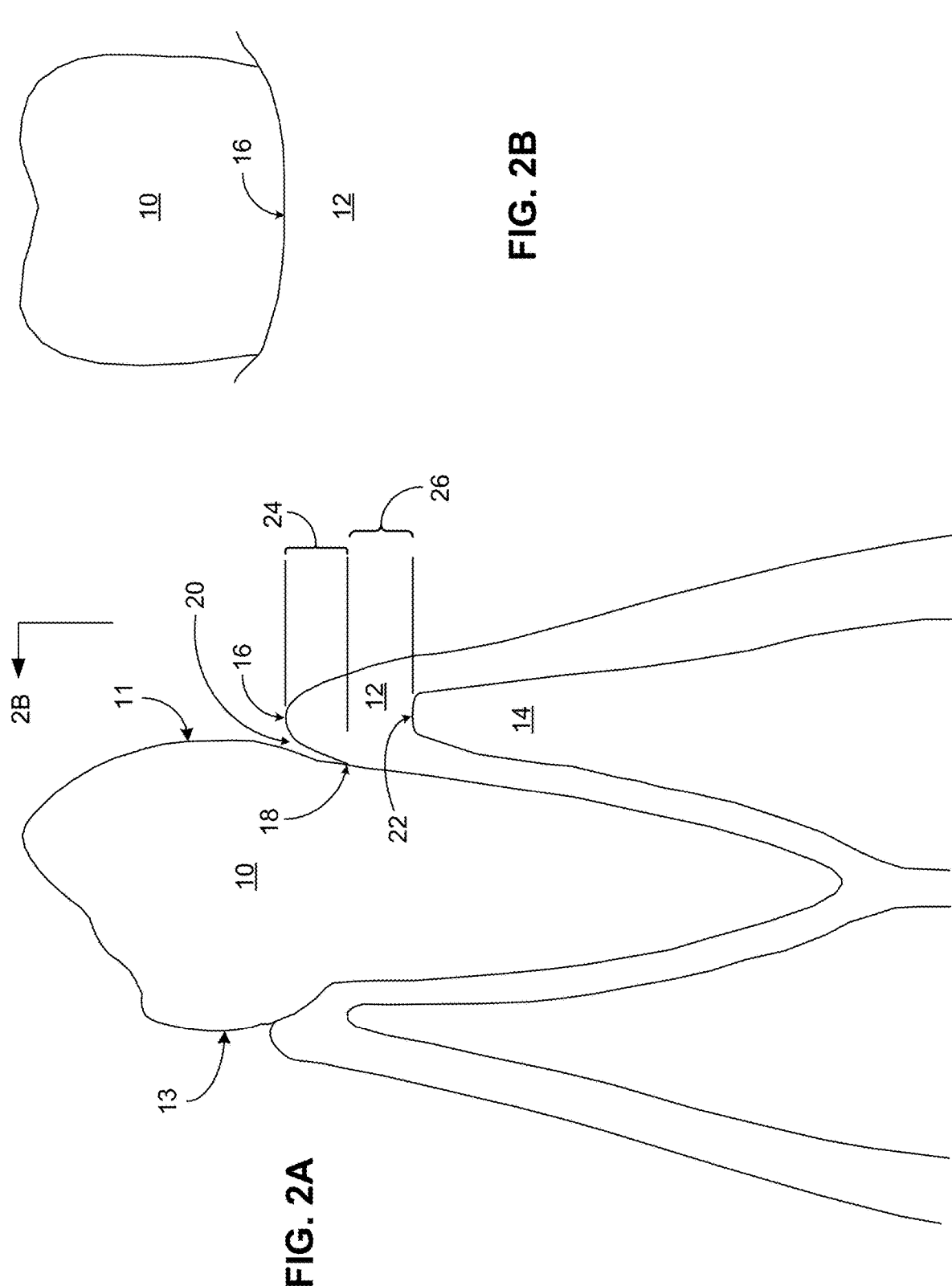
FIG. 2A shows a side sectional view of a tooth having a moderate level of periodontitis associated with a gum tissue.
FIG. 2B shows a front view of the tooth of FIG. 2A.
Figures 3A, 3B:
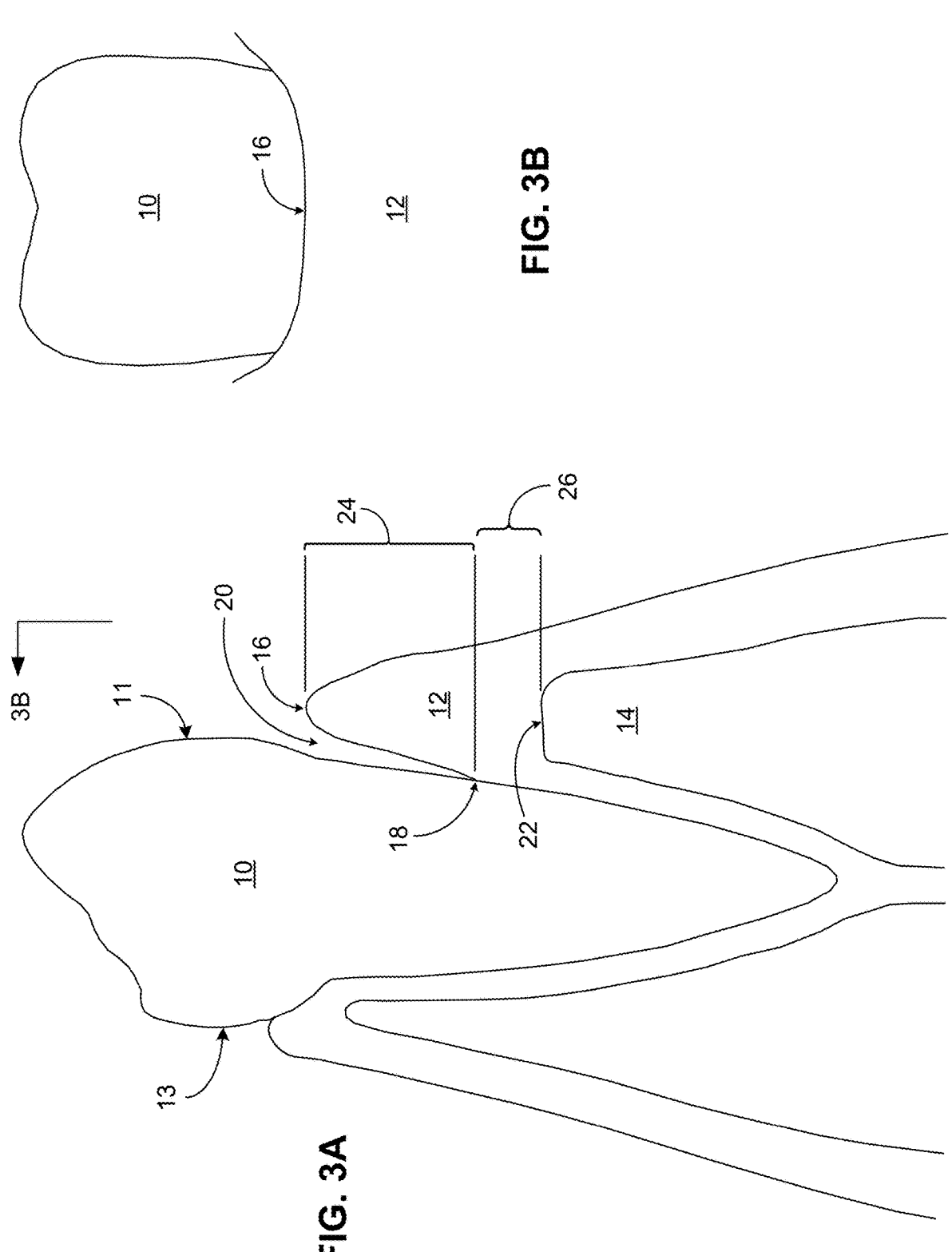
FIG. 3A shows a side sectional view of a tooth having a more severe level of periodontitis associated with a gum tissue.
FIG. 3B shows a front view of the tooth of FIG. 3A.

FIGS. 1 to 3 depict various conditions of a gum tissue 12 associated with a corresponding tooth 10. For the example tooth 10, its buccal and lingual sides are indicated as 11 and 13, respectively. FIG. 1A shows a side sectional view of a tooth 10 having a healthy gum tissue 12 with a gumline indicated as 16; and FIG. 1B shows a front view (showing the buccal side) of the tooth 10 of FIG. 1A. FIG. 2A shows a side sectional view of a tooth 10 having a moderate level of periodontitis associated with a gum tissue 12 with a gumline indicated as 16; and FIG. 2B shows a front view (showing the buccal side) of the tooth 10 of FIG. 2A. FIG. 3A shows a side sectional view of a tooth 10 having a more severe level of periodontitis associated with a gum tissue 12 with a gumline indicated as 16; and FIG. 3B shows a front view (showing the buccal side) of the tooth 10 of FIG. 3A.

In the example of FIG. 1A, the gum tissue 12 and the tooth 10 are shown to define a pocket 20 having a base 18. Accordingly, such a pocket has a pocket depth, indicated as 24, that is equal to or proportional to a distance between the gumline 16 and the base 18.

Referring to FIG. 1A, a bone structure 14 that supports the tooth 10 is shown to include a top portion 22 associated with the pocket 20. Thus, dimension indicated as 26 is equal to or proportional to a distance between the base 18 of the pocket 20 and the top portion 22 of the bone structure 14.

Similarly, in each of the examples of FIGS. 2A and 3A, the respective gum tissue 12 and the tooth 10 are shown to define a corresponding pocket 20 having a base 18, such that the pocket 20 has a pocket depth, indicated as 24, that is equal to or proportional to a distance between the gumline 16 and the base 18. Similarly, a respective bone structure 14 that supports the corresponding tooth 10 is shown to include a top portion 22 associated with the pocket 20. Thus, respective dimension indicated as 26 is equal to or proportional to a distance between the base 18 of the pocket 20 and the top portion 22 of the bone structure 14.

In the examples of FIGS. 1 to 3, the respective gum tissue conditions are depicted for the buccal side; however, it will be understood that the gum tissues on the lingual side may have similar conditions.

Figure 4:
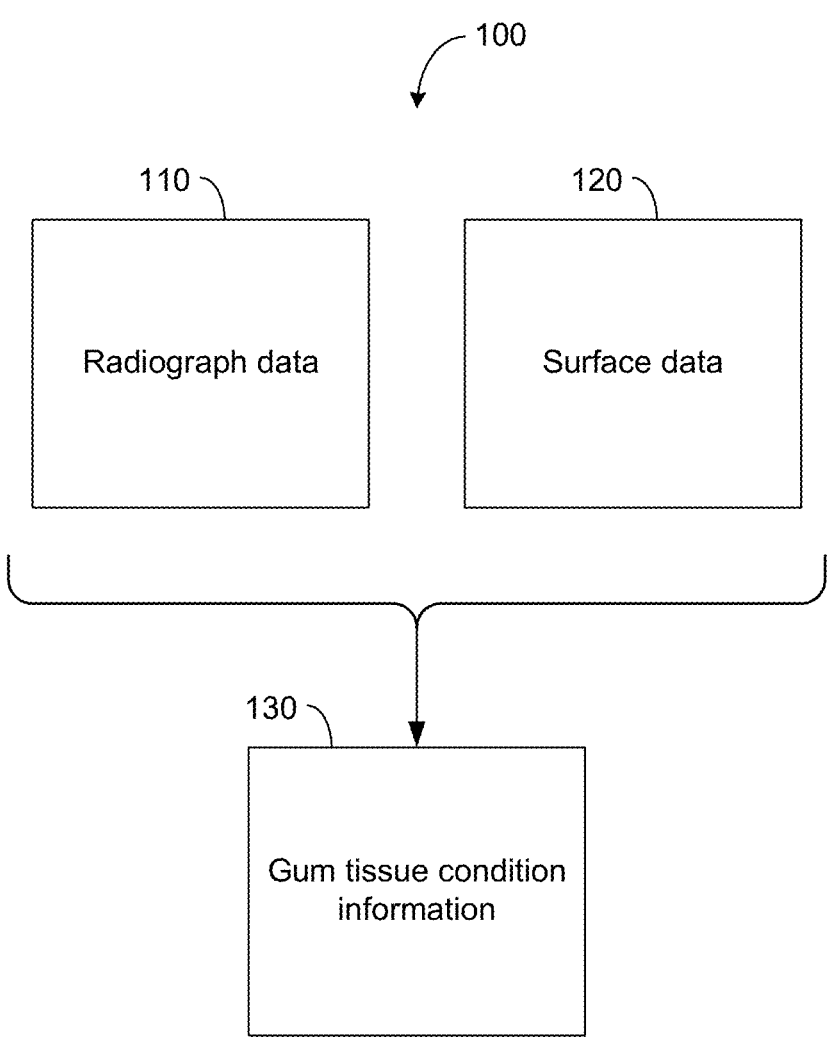
FIG. 4 shows that on some implementations, a system can be implemented to combine radiographic data associated with a tooth and surface data associated with the tooth to generate information representative of one or more conditions of gum tissue associated with the tooth.

FIG. 4 shows that on some implementations, a system 100 can be implemented to combine radiographic data 110 associated with a tooth and surface data 120 associated with the tooth to generate information 130 representative of one or more conditions of gum tissue associated with the tooth. In some embodiments, such a system can be configured to obtain gum tissue condition information for one tooth or a plurality of teeth. For the latter example, the plurality of teeth can include, for example, all of the teeth for a given patient.

In some embodiments, the gum tissue condition information 130 of FIG. 4 can include information representative of gum pocket depth, gum recession and/or gum thickness.

Examples related to such gum tissue conditions are described herein in greater detail.

Figure 5:
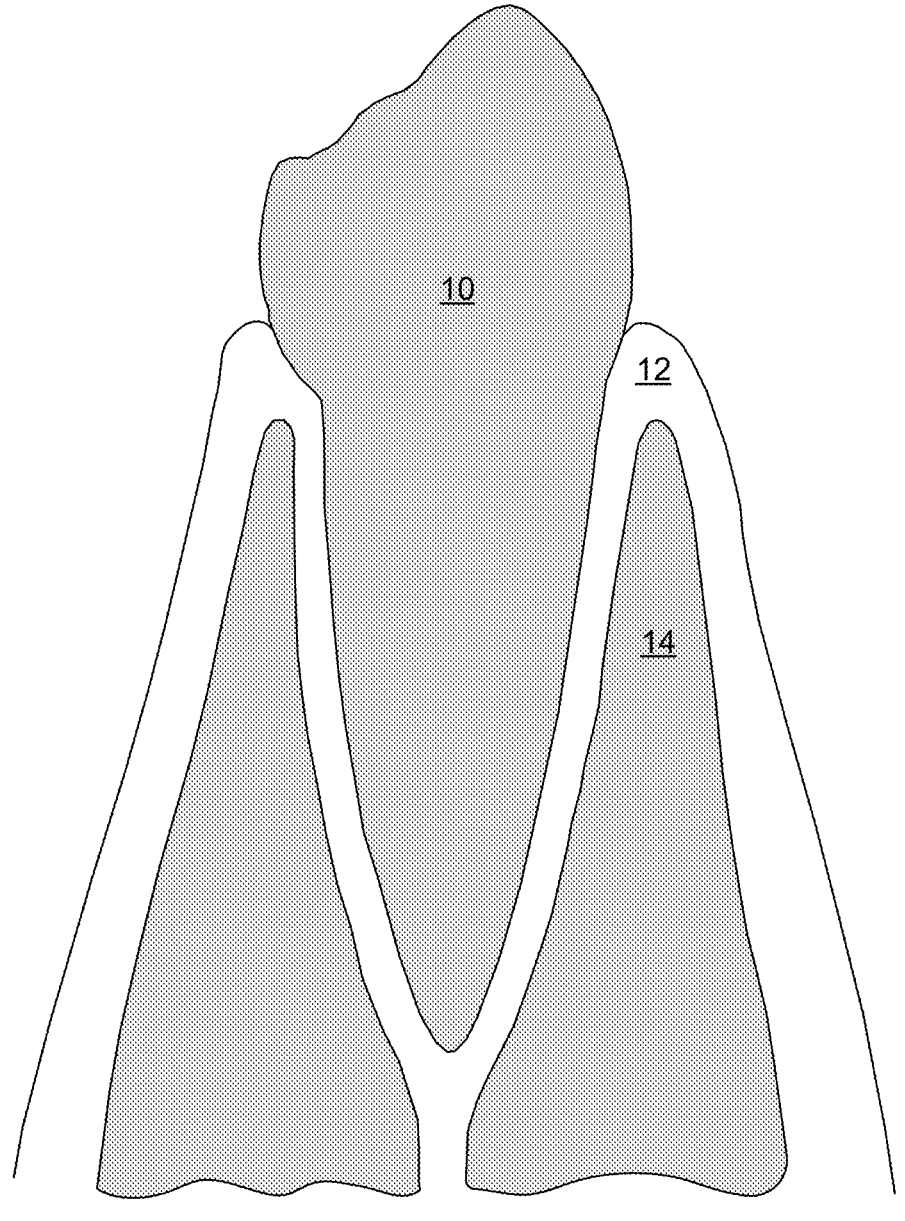
FIG. 5 depicts a side view of a tooth similar to the tooth of FIG. 1A, where a radiograph of such a tooth can provide an image of more dense materials such as the tooth and the bone structure.

FIG. 5 depicts a side view of a tooth 10 similar to the tooth 10 of FIG. 1A. A radiograph of such a tooth can provide an image of more dense materials such as the tooth 10 and the bone structure 14. In FIG. 5, such dense materials are depicted as shaded portions, while the gum tissue 12 having less dense material likely will be transparent or not provide a clear image in the radiograph.

Figures 6A, 6B, 6C:
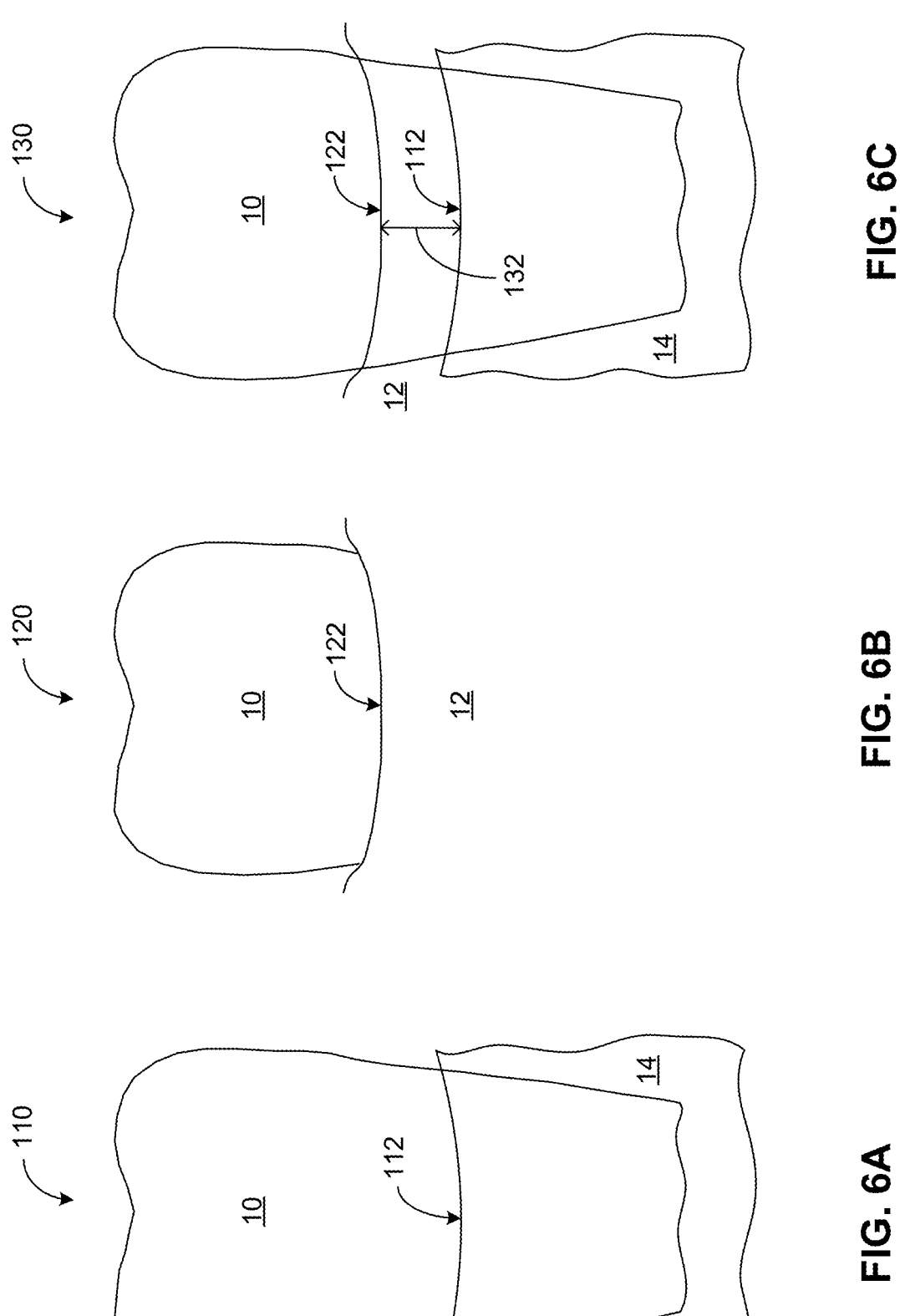
FIG. 6A depicts a front view of a radiograph of the tooth of FIG. 5.
FIG. 6B depicts a similar view of a surface image of the tooth of FIG. 6A.
FIG. 6C depicts a combination of the radiograph of FIG. 6A and the surface image of FIG. 6B.

FIG. 6A shows a front view (e.g., a buccal-side view) of a radiograph 110 of the tooth 10 of FIG. 5. In such a radiograph, the tooth 10 and the bone structure 14 are shown to be identifiable. Also identifiable is a top portion 112 of the bone structure 14. It is noted that in the example radiograph 110 of FIG. 6A, other less-dense features (e.g., gum tissue) are not depicted. Accordingly, such a radiograph itself typically does not provide useful information with respect to less-dense features such as gum tissue.

FIG. 6B shows a similar view of a surface image 120 of the tooth 10 of FIG. 6A. In such a surface image, surface features of the tooth 10 and the gum tissue 12 are identifiable. Also identifiable is a gumline 122 of the gum tissue 12. It is noted that in the example surface image 120 of FIG. 6B, information associated with sub-surface features (e.g., bone structure 14 in FIG. 6A) are generally not available.

FIG. 6C depicts a combination 130 of the radiograph 110 of FIG. 6A and the surface image 120 of FIG. 6B. In such a combination, information associated with sub-surface features (e.g., bone structure 14 in FIG. 6A) and information associated with surface features (e.g., gum tissue 12 in FIG. 6B) are available.

FIG. 6C shows that in some embodiments, one or more dimensions associated with the gum tissue 12 can be obtained from the information provided by the combination 130 of the radiograph 110 of FIG. 6A and the surface image 120 of FIG. 6B. For example, a distance indicated as 132 between the gumline 122 and the top portion 112 of the bone structure 14 can be obtained. Examples of how such distance information can be utilized are described herein in greater detail.

It is noted that the radiograph 110 of FIG. 6A can be an example of the radiograph data 110 of the system 100 of FIG. 4. Similarly, the surface image 120 of FIG. 6B can be an example of the surface data 120 of the system 100 of FIG. 4. The combination 130 of FIG. 6C can be an example of the gum tissue condition information 130 of the system 100 of FIG. 4.

In some embodiments, a system having one or more features as described herein can be configured to generate gum tissue condition information (130 in FIGS. 4 and 6C) from corresponding radiograph data and surface data, without any additional data or information.

In some embodiments, a system having one or more features as described herein can be configured to generate gum tissue condition information (130 in FIGS. 4 and 6C) from corresponding radiograph data and surface data, with additional data or information.

For example, such additional data or information can include a biologic width associated with a tooth. In some embodiments, a pocket depth of a corresponding gum tissue can be calculated by determining relative positions of gumline (e.g., 122 in FIG. 6C) and top portion (e.g., 112 in FIG. 6C) of the bone structure 14 to provide a distance (132 in FIG. 6C) between the gumline 122 and the top portion 112 of the bone structure 14. The biologic width associated with the tooth (10 in FIG. 6C) and the gum tissue (12 in FIG. 6C) is approximately a distance between the top portion 112 of the bone structure 14 and the base of a pocket defined by the tooth 10 and the gum tissue 12. Thus, depth of such a pocket can be calculated by subtracting the biologic width dimension from the dimension 132 (between the gumline 122 and the top portion 112 of the bone structure 14).

Figures 7A, 7B, 7C:
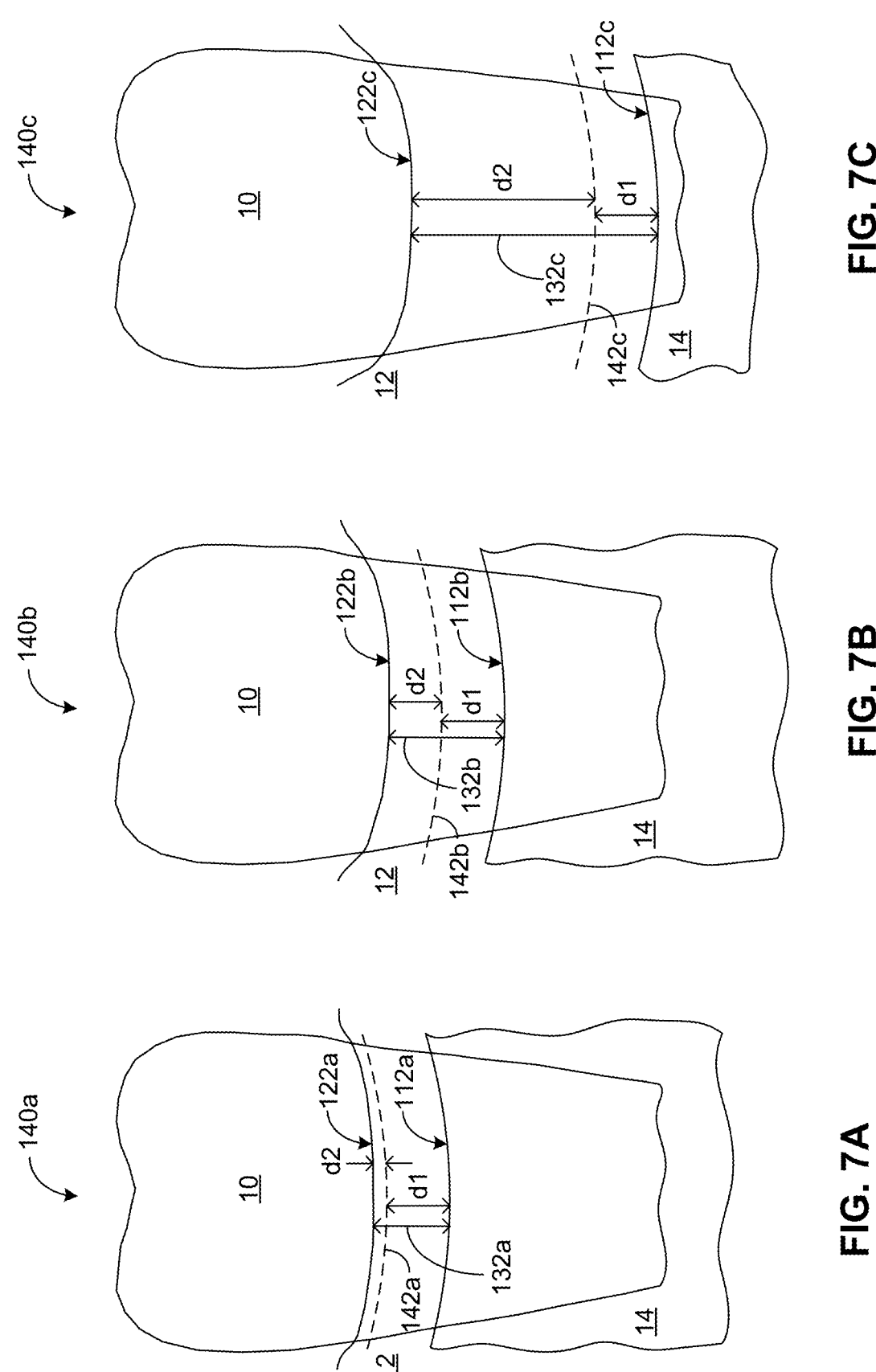
FIGS. 7A to 7C depict examples of pocket depths (indicated as d2) calculated as described herein, for the three example gum tissue conditions of FIGS. 1 to 3.

FIGS. 7A to 7C show examples of pocket depths (indicated as d2) calculated as described above, for the three example gum tissue conditions of FIGS. 1 to 3. In the example of FIG. 7A, gum tissue condition information (130 in FIG. 4) can include pocket depth information 140a, where a pocket depth d2 is obtained based on a dimension 132a (between a gumline 122a and a top portion 112a of a corresponding bone structure 14) and a biologic width dimension d1. Similarly, in the example of FIG. 7B, gum tissue condition information (130 in FIG. 4) can include pocket depth information 140b, where a pocket depth d2 is obtained based on a dimension 132b (between a gumline 122b and a top portion 112b of a corresponding bone structure 14) and a biologic width dimension d1. Similarly, in the example of FIG. 7C, gum tissue condition information (130 in FIG. 4) can include pocket depth information 140c, where a pocket depth d2 is obtained based on a dimension 132c (between a gumline 122c and a top portion 112c of a corresponding bone structure 14) and a biologic width dimension d1.

In some embodiments, a system having one or more features as described herein can utilize a constant value for a biologic width dimension (d1) associated with a tooth at different gum tissue conditions. In such a system, the dimensions d1 of the different gum tissue conditions of FIGS. 7A to 7C can be approximately the same. Such a constant value for the dimension d1 can be, for example, approximately 2 mm. In such an example, the pocket depth d2 in FIG. 7A can be calculated as the dimension 132a minus 2 mm; the pocket depth d2 in FIG. 7B can be calculated as the dimension 132b minus 2 mm; and the pocket depth d2 in FIG. 7C can be calculated as the dimension 132c minus 2 mm.

As described herein, pocket depth can be obtained at each of a plurality of locations around a given tooth. In some embodiments, each of such pocket depth values can be obtained with a constant biologic width value (e.g., 2 mm).

As described herein, pocket depth can be obtained at one or more locations around each of a plurality of teeth of a patient. For example, pocket depths can be calculated as described herein for an entire set of teeth of a patient. For such calculations of pocket depths, a constant biologic width value (e.g., 2 mm) can be utilized for each tooth in the set of teeth.

It is noted that in some embodiments, a system having one or more features as described herein can utilize biologic width values that are not necessarily a constant value. For example, a value of biologic width may depend on a location of a given tooth, on a type of tooth in a given set of teeth, on a patient, or some combination thereof. Some or all of such dependence of biologic width may be obtained from, for example, separate measurements on one or more teeth of the patient, some average biologic values associated with similar teeth, similar demographics, or some combination thereof.

Figure 8A:
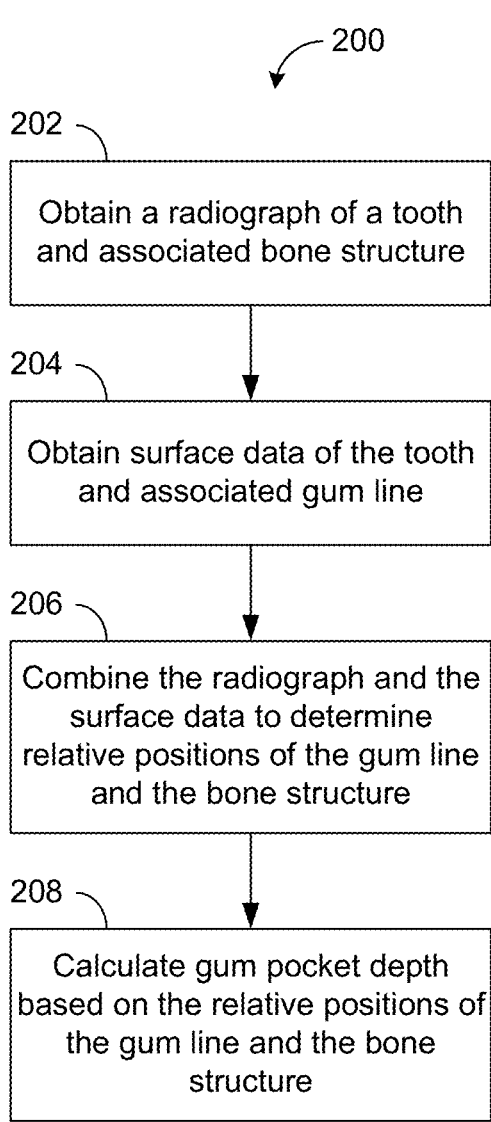
FIG. 8A shows a process that can be implemented by a system having one or more features as described herein.

FIG. 8A shows a process 200 that can be implemented by a system having one or more features as described herein. In process block 202, a radiograph of a tooth and associated bone structure can be obtained. In process block 204, surface data of the tooth and associated gum line can be obtained. In process block 206, the radiograph and the surface data can be combined to determine relative positions of the gum line and the bone structure. In process block 208, a gum pocket depth associated with the tooth can be calculated based on the relative positions of the gum line and the bone structure.

In some embodiments, the radiograph of FIGS. 4 and 8A can be a cone beam computed tomography (CBCT) radiograph of some or all of a mouth of a patient, and the surface data of FIGS. 4 and 8A can be a scan data (e.g., an intraoral scanner data) of a corresponding portion of the mouth of the patient.

It is noted that a CBCT device can generate CT scans while utilizing less radiation being delivered to a patient, due to the radiation beam is confined to a cone shape. Such a CBCT radiograph can provide a 3-dimensional rendering of the teeth and related bone structures of the entire mouth.

It is also noted that an intraoral scanner can generate digital impressions of teeth which can be used for various dental applications such as orthodontics, crown fabrication and implant guide printing. Such an intraoral scanner can obtain images of the teeth and gums, and such images can be processed to provide 3-dimensional rendering or model.

Figure 8B:
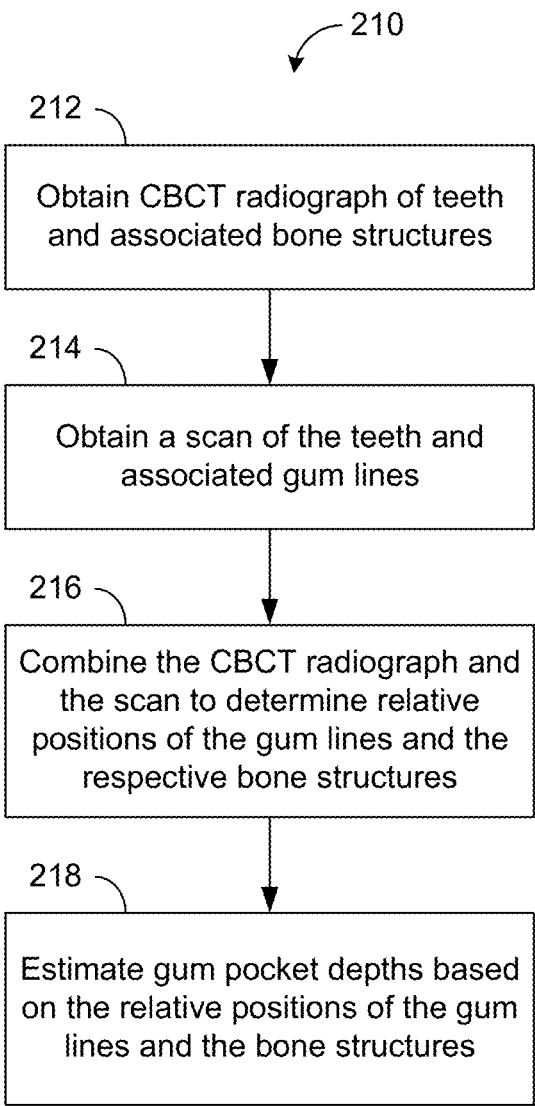
FIG. 8B shows a process that can be implemented as a more specific example of the process of FIG. 8A.

Accordingly, FIG. 8B shows a process 210 that can be implemented as a more specific example of the process 200 of FIG. 8A. In process block 212, a CBCT radiograph of teeth and associated bone structures can be obtained. In process block 214, scan data of the teeth and associated gum lines can be obtained. In process block 216, the CBCT radiograph and the scan data can be combined to determine relative positions of the gum lines and the respective bone structures. In process block 218, gum pocket depths associated with the teeth can be calculated based on the relative positions of the gum lines and the respective bone structures.

In some embodiments, the combining process block 216 can include merging or superimposing of the bone imaging data from the CBCT radiograph and imaging scan of the gums (including the respective gum lines). Such merging or superimposing of the two sets of data can be facilitated by matching one or more markers or features that are unique to the set of teeth. In some embodiments, some or all of such unique markers or features can be the same ones that would be utilized as, for example, implant guides.

Figure 9A:
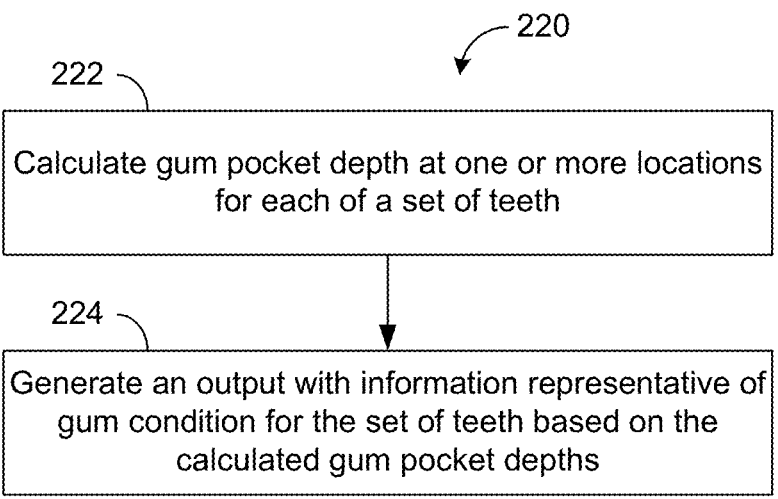
FIG. 9A shows a process that can be implemented to calculate one or more gum pocket depths associated with a tooth, and generate an output representative of gum condition of the tooth.

FIG. 9A shows a process 220 that can be implemented to calculate one or more gum pocket depths associated with a tooth, such as in the process block 208 of FIG. 8A, and generate an output representative of gum condition of the tooth. In process block 222, gum pocket depth can be calculated at one or more locations for each tooth of a set of teeth. In block 224, an output with information representative of gum condition for the set of teeth can be generated based on the calculated gum pocket depths.

Figure 10:
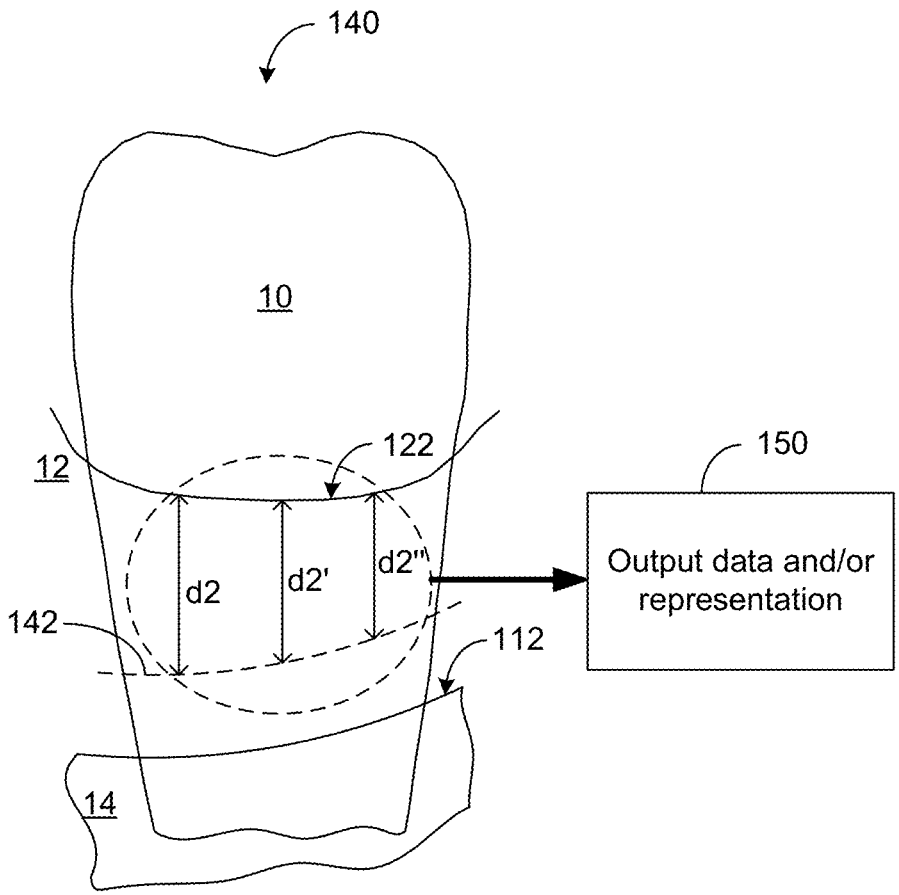
FIG. 10 shows an example of gum pocket depth information being obtained and an output being generated based on the gum pocket depth information.

FIG. 10 shows an example of gum pocket depth information 140 being obtained (e.g., as in the process 220 of FIG. 9A) and an output 150 being generated based on the gum pocket depth information. In the example of FIG. 10, a plurality of gum depth values (e.g., d2, d2', d2") can be obtained as described herein for a given tooth 10, based on identification of a bone feature 112 of a bone structure 14 and a gum line 122. Such calculated gum depth values can be included in the output 150 in the form of data and/or representation of health condition of the gum 12.

It is noted that in the example of FIG. 10, gum pocket depth values are obtained at a plurality of discrete locations. It will be understood that in some embodiments, continuous or approximately continuous profile 142 of the base of the gum pocket can be generated based on the identified bone feature 112 (e.g., by adding a biologic width to the profile of the bone feature 112. In such an implementation, pocket depth can be calculated anywhere along the pocket-base profile 142 since the gum line 122 has been identified.

Figure 11A:
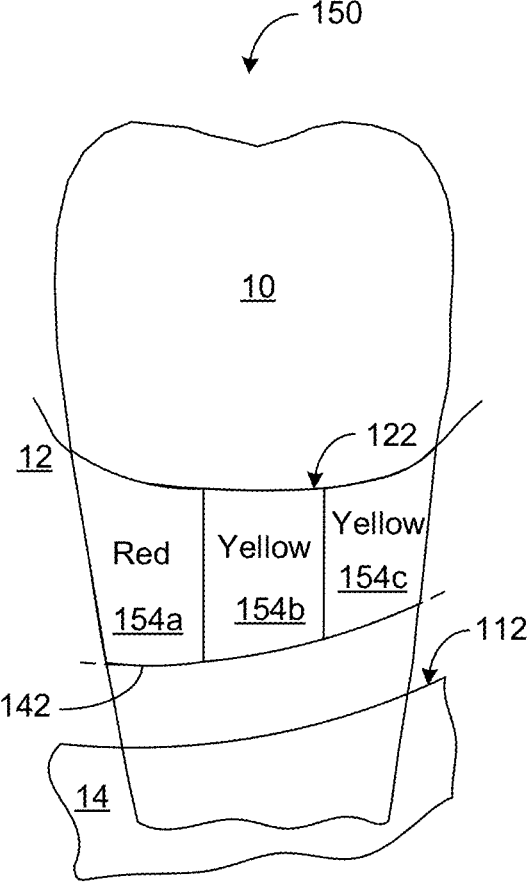
FIG. 11A shows that in some embodiments, an output generated based on gum pocket depth information can include visual display representative of the measured pocket depth values.
Figure 11B:
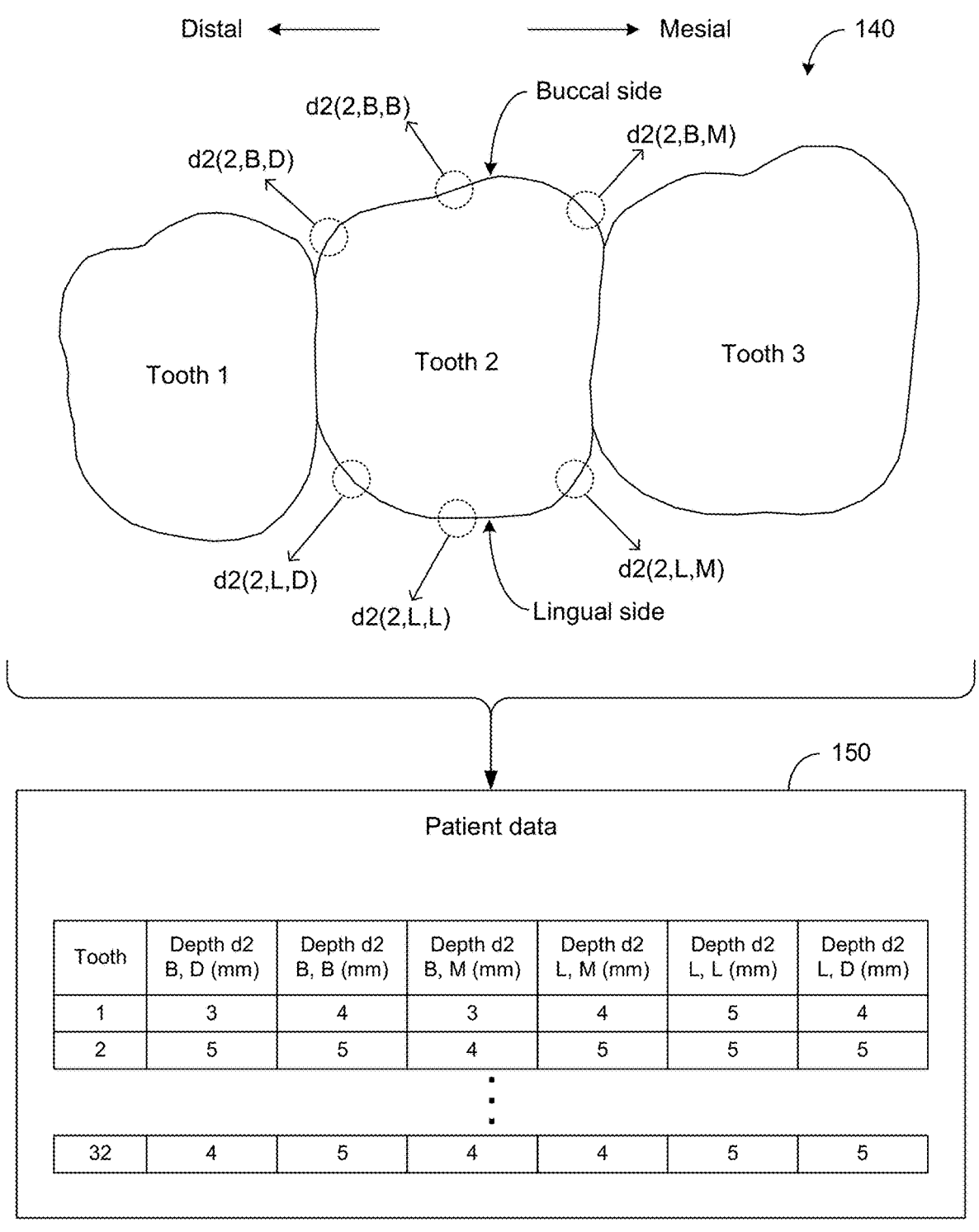
FIG. 11B shows an example of an output generated from gum pocket depth information obtained as described herein.

FIGS. 11A and 11B show examples of how the output 150 of FIG. 10 can be implemented. FIG. 11A shows that in some embodiments, an output 150 generated based on gum pocket depth information can include visual display representative of the measured pocket depth values. For example, suppose that in the example of FIG. 10, the measured pocket depth d2 is in a range characteristic of severe gum disease condition, and each of the measured pocket depths d2' and d2" is in a range characteristic of moderate gum disease condition. Based on such example classification, an area of the gum 12 can be color coded in a visual display. For example, an area 154a having a severe gum disease condition as measured by the pocket depth d2 can be provided with a red color, and each of areas 154b and 154c having moderate gum disease condition as measured by the respective pocket depths d2' and d2" can be provided with a yellow color.

In some applications, it may be preferable to include pocket depth values in an output (150 in FIG. 10), so that such values can become part of a patient's chart. FIG. 11B shows an example of such an output (150) generated from gum pocket depth information 140 obtained as described herein. In the example of FIG. 11B, six gum pocket depth measurements are obtained at six locations about a given tooth commonly probed in a periodontal probing process, so as to allow the six gum pocket depth measurements to be included in a common format of a patient chart.

Referring to FIG. 11B, the six example pocket depth measurements are shown to be obtained for a tooth having a number (e.g., Tooth 2) at buccal distal location (B, D), buccal middle location (B, B), buccal mesial location (B, M), lingual distal location (L, D), lingual middle location (L, L), and lingual mesial location (L, M). Accordingly, corresponding six data values for Tooth 2 can be represented as d2(2, B, D), d2(2, B, B), d2(2, B, M), d2(2, L, D), d2(2, L, L), and d2(2, L, M), respectively, where the first index 2 represents Tooth 2.

In the example of FIG. 11B, such data values and values for other teeth are shown to be included in patient data 150. For example, Tooth 2 is shown to have measured pocket depth values of 5 mm, 5 mm, 4 mm, 5 mm, 5 mm, and 5 mm at the six locations.

Figure 9B:
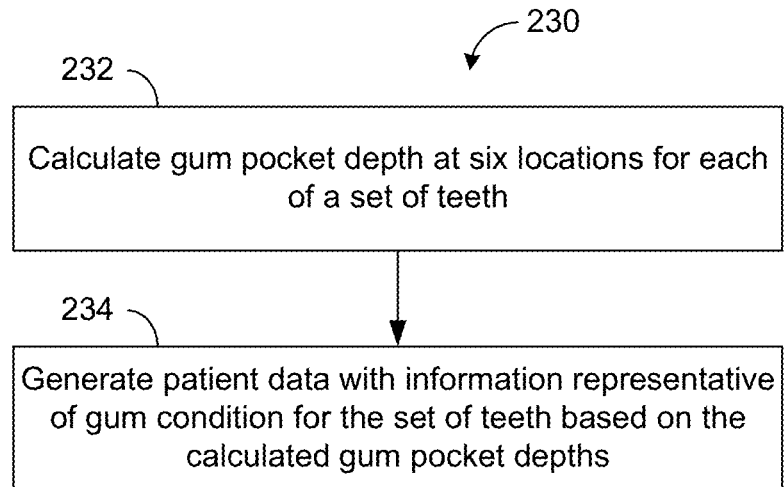
FIG. 9B shows a process that can be implemented as a more specific example of the process of FIG. 9A.

To generate the patient data 150 of FIG. 11B, a process 230 of FIG. 9B, which is a more specific example of the process 220 of FIG. 9A, can be implemented. In process block 232, gum pocket depth values can be calculated at locations including six commonly probed locations for each of a set of teeth. In process block 234, patient data can be generated to include information representative of gum conditions for the set of teeth, based on the calculated gum pocket depths.

In the various examples described herein in reference to FIGS. 7 to 11, radiograph data (110 in FIG. 4) and surface data (120 in FIG. 4) are combined with additional information (e.g., biologic width) to generate gum condition related information such as gum depth information. In some embodiments, a system having one or more features as described herein can be configured to generate gum condition related information without use of additional information that is not available in radiograph data and surface data.

Figure 12:
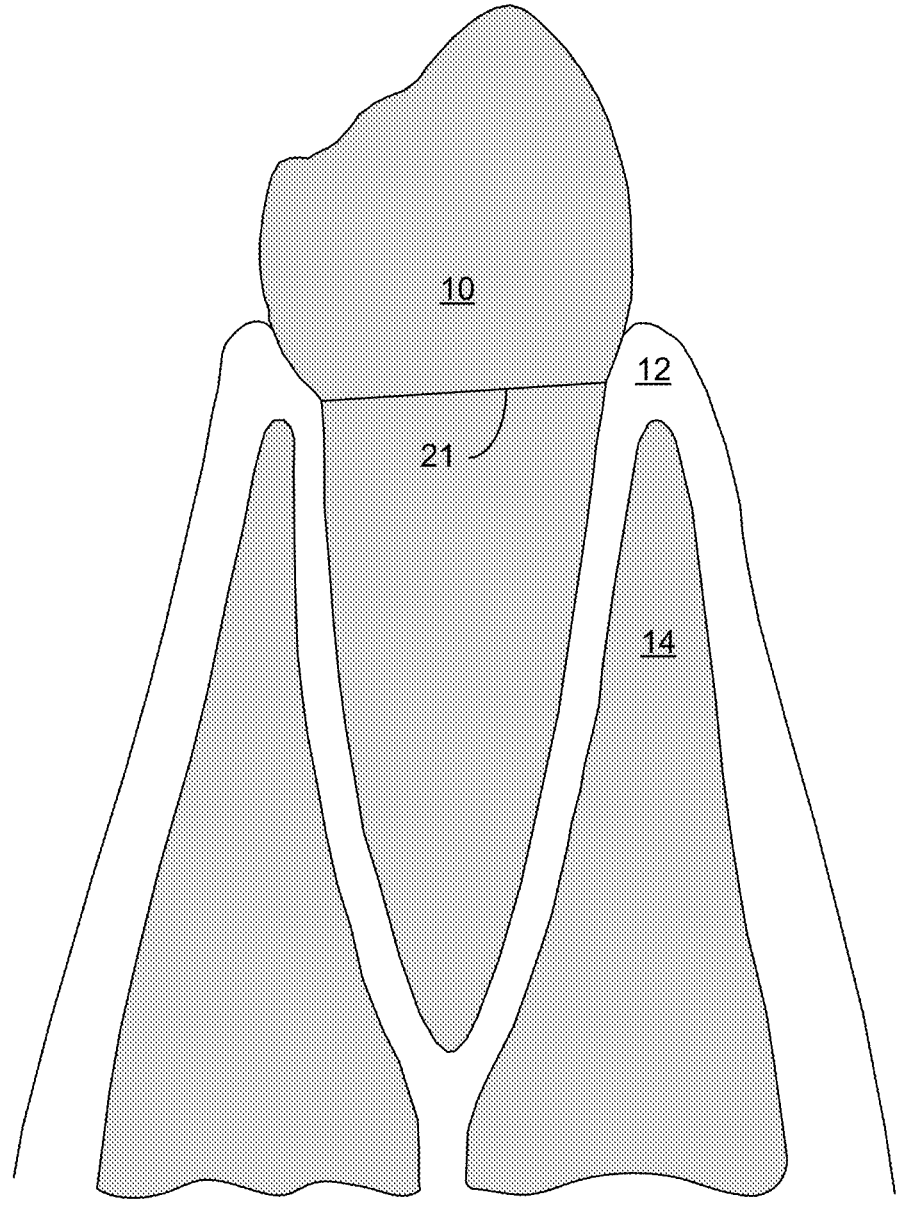
FIG. 12 shows a side view of a tooth similar to the tooth of FIG. 5.

For example, FIG. 12 shows a side view of a tooth 10 similar to the tooth 10 of FIG. 5. A radiograph of such a tooth can provide an image of more dense materials such as the tooth 10 and the bone structure 14. In FIG. 12, such dense materials are depicted as shaded portions, while the gum tissue 12 having less dense material likely will be transparent or not provide a clear image in the radiograph. In such a radiograph, a cemento enamel junction (CEJ) 21 where the root meets the enamel can be identified.

Figures 13A, 13B, 13C:
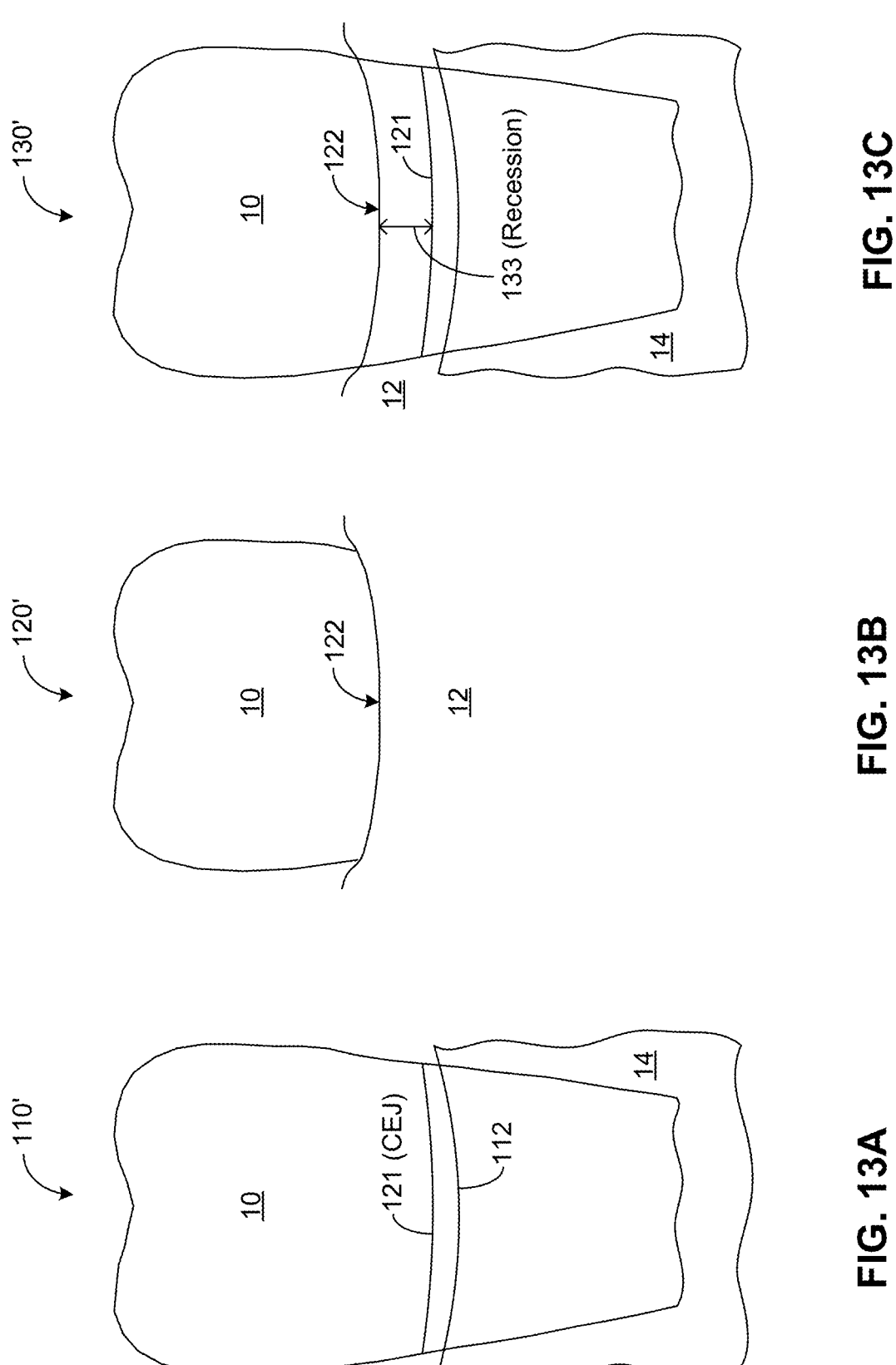
FIG. 13A shows a front view of a radiograph of the tooth of FIG. 12.
FIG. 13B shows a similar view of a surface image of the tooth of FIG. 13A.
FIG. 13C depicts a combination of the radiograph of FIG. 13A and the surface image of FIG. 13B.

FIG. 13A shows a front view (e.g., a buccal-side view) of a radiograph 110' of the tooth 10 of FIG. 12. In such a radiograph, the tooth 10 and the bone structure 14 are shown to be identifiable. Also identifiable is a top portion 112 of the bone structure 14, and a cemento enamel junction (CEJ) 121.

FIG. 13B shows a similar view of a surface image 120' of the tooth 10 of FIG. 13A. In such a surface image, surface features of the tooth 10 and the gum tissue 12 are identifiable. Also identifiable is a gumline 122 of the gum tissue 12.

FIG. 13C depicts a combination 130' of the radiograph 110' of FIG. 13A and the surface image 120' of FIG. 13B. In such a combination, information associated with sub-surface features (e.g., bone structure 14 and CEJ 121 in FIG. 13A) and information associated with surface features (e.g., gum tissue 12 and gumline 122 in FIG. 13B) are available.

FIG. 13C shows that in some embodiments, one or more dimensions associated with the gum tissue 12 can be obtained from the information provided by the combination 130' of the radiograph 110' of FIG. 13A and the surface image 120' of FIG. 13B. For example, a distance indicated as 133 between the gumline 122 and the CEJ 121 can be obtained. Such a distance (133) is representative of gum recession which is the distance between the CEJ 121 and the gumline 122.

It is noted that measurement of gum recession can be important, since a tooth may have a shallow pocket depth but still need attention because of the recession of the gum.

Figure 14:
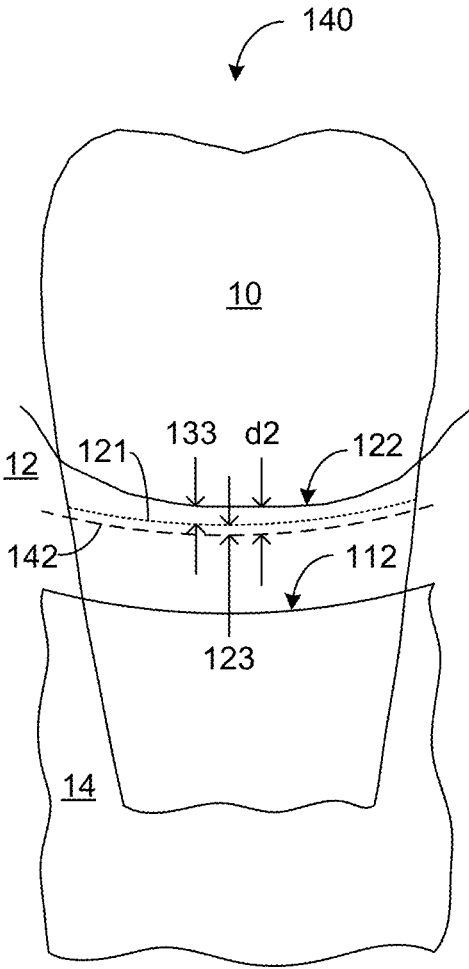
FIG. 14 shows that in some embodiments, a number of tooth-related parameters can be obtained utilizing one or more features as described herein.

FIG. 14 depicts pocket depth information 140 similar to the examples of FIGS. 7A to 7C, where gumline 122, gum pocket base profile 142, and bone feature 112 are identified to allow calculation of pocket depth d2. It is noted that the gum base profile 142 can be obtained by use of biologic width information as described herein.

In the example of FIG. 14, CEJ 121 is also identified, similar to the example of FIG. 13C to allow calculation of gum recession dimension 133. In some embodiments, clinical attachment level (CAL), indicated as 123, can be measured as a distance between the CEJ 121 and the pocket base 142. It is noted that such measurement of CAL can be representative of loss of clinical attachment of the gum to the tooth.

Figure 15:
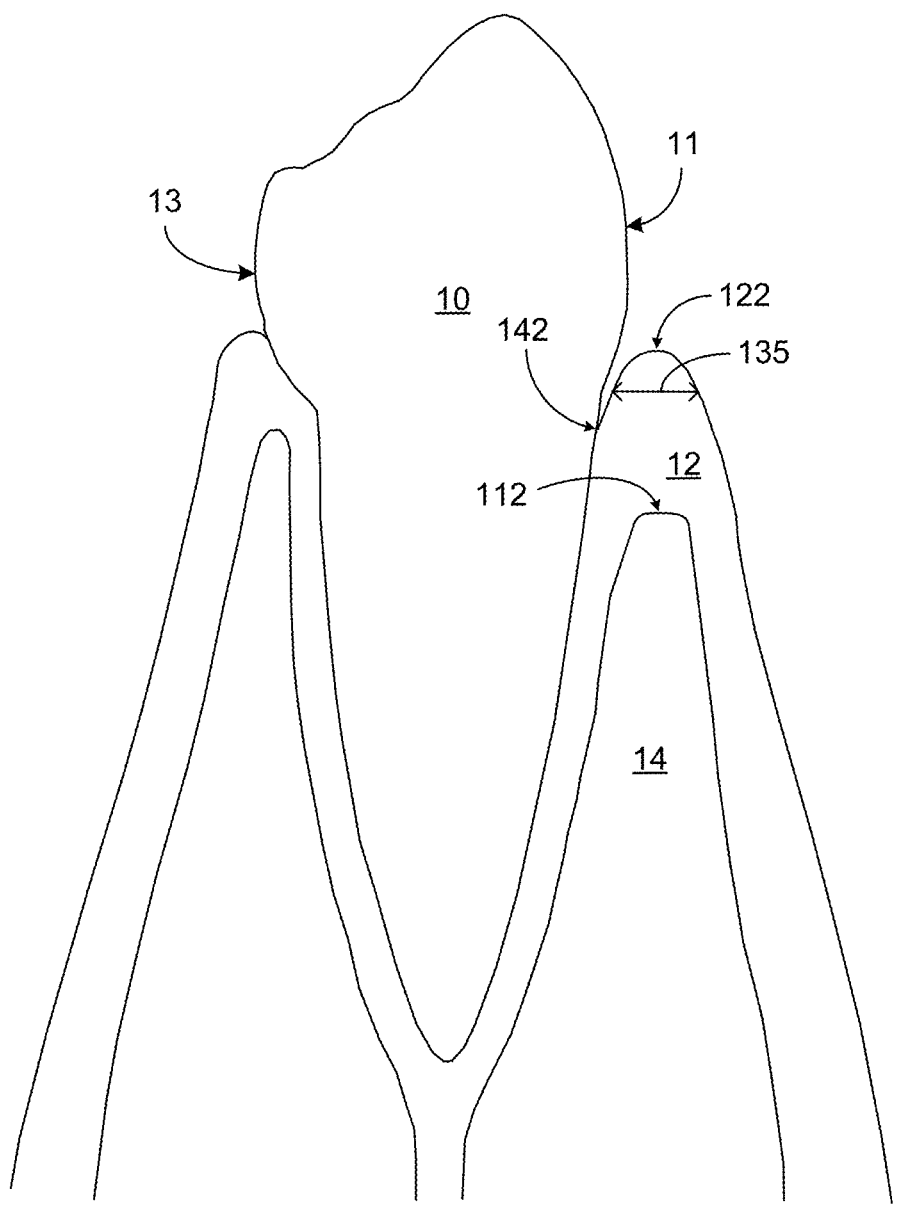
FIG. 15 depicts a side view of a tooth similar to the tooth of FIG. 5, with a pocket base identified with respect to the corresponding gum tissue.

FIG. 15 depicts a side view of a tooth 10 similar to the tooth 10 of FIG. 5. In the example of FIG. 14, pocket base profile 142 can be identified by a system having one or more features as described herein. In FIG. 15, such a pocket base is indicated as 142 with respect to the corresponding gum tissue 12.

In some embodiments, one or more gum thickness values can be obtained from some or all of the identified features of the gum tissue 12. For example, a gum thickness dimension indicated as 135 can be a thickness between the exterior of the gum tissue 12 and the interior side defining the pocket. Such a thickness can be obtained at, for example, mid-height between the gum base 142 and the gumline 122.

It is noted that the foregoing gum thickness can provide measurement of biotype that can be an indication of gum condition. For example, if a gum tissue associated with a pocket is thicker than 1.5 mm, it is considered to be "thick"; and if it is thinner than 1.5 mm it is "thin." Such thickness information can be utilized to assess the risk of recession resulting from, for example, normal aging and/or after a procedure such as an implant.

As described herein, data having a combination of radiograph data such as CBCT data and surface data such as intraoral scan data can be utilized to obtain one or more measurement(s) that is/are indicative of periodontal condition of the teeth of a patient. In some embodiments, one or more features of the present disclosure can also be utilized to obtain periodontal condition of a patient by a combination of measurements or observations where at least one of such measurements or observations is obtainable from one of radiograph data and surface data without the use of the other.

For example, and as shown in FIG. 13A, radiograph 110' can provide identifiable features such as a top portion 112 of the bone structure 14, and a CEJ 121. With such identified features, a distance between the CEJ 121 and the top portion 112 of the bone structure can provide information about alveolar crest height of the bone structure 14. In some embodiments, such information can be utilized by itself or in combination with one or more measurements or observations as described herein to obtain improved characterization of periodontal condition of the patient.

In another example, features such as gumline profile, gum inflammation and/or abfraction may be measurable or observable in surface data. In some embodiments, some or all of such information can be utilized by itself or in combination of one or more measurements or observations as described herein to obtain improved characterization of periodontal condition of the patient.

FIG. 16A shows a process 300 that can be implemented by a system having one or more features as described herein. In process block 302, a radiograph of a tooth and associated bone structure can be obtained. In process block 304, surface data of the tooth and associated gum line can be obtained. In process block 306, the radiograph and the surface data can be combined to determine one or more of (a) relative positions of the gum line and the bone structure, (b) relative positions of the gum line and CEJ, and (c) sectional gum profile. In process block 308, one or more of (a) gum pocket depth based on the relative positions of the gum line and the bone structure, (b) gum recession based on the relative positions of the gum line and the CEJ, and (c) gum thickness based on the sectional gum profile can be calculated.

FIG. 16B shows a process 310 that can be a more specific example of the process 300 of FIG. 16A. In process block 312, a CBCT radiograph of a tooth and associated bone structure can be obtained. In process block 314, scan data of the tooth and associated gum line can be obtained. In process block 316, the CBCT radiograph and the scan data can be combined to determine one or more of (a) relative positions of the gum line and the bone structure, (b) relative positions of the gum line and CEJ, and (c) sectional gum profile. In process block 318, one or more of (a) gum pocket depth based on the relative positions of the gum line and the bone structure, (b) gum recession based on the relative positions of the gum line and the CEJ, and (c) gum thickness based on the sectional gum profile can be calculated.

Figure 17:
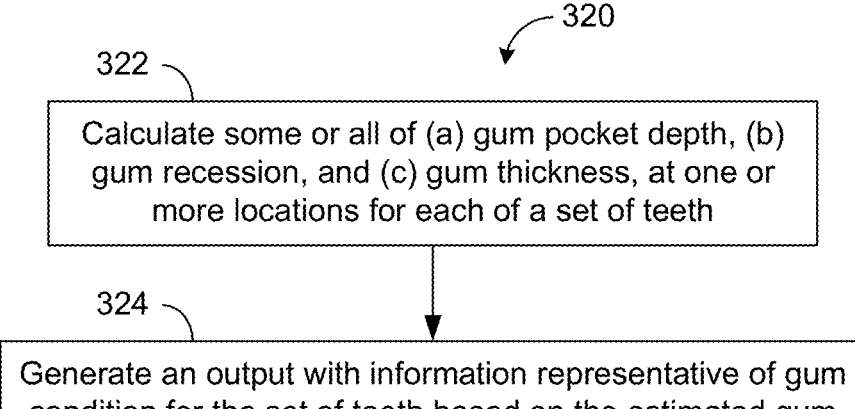
FIG. 17 shows a process that can be implemented to calculate some or all of (a) gum pocket depth, (b) gum recession, and (c) gum thickness, at one or more locations for each of a set of teeth.

FIG. 17 shows a process 320 that can be implemented to calculate some or all of (a) gum pocket depth, (b) gum recession, and (c) gum thickness, at one or more locations for each of a set of teeth. In block 324, an output with information representative of gum condition for the set of teeth can be generated based on the estimated gum pocket depths, gum recessions, and/or gum thicknesses.

In some implementations, the present disclosure relates to a method for measuring condition of gum tissue, where the method can include generating or obtaining radiograph data for a tooth and a respective bone structure; generating or obtaining surface data for the tooth, with the surface data including surface information of a gum tissue associated with the tooth; combining the radiograph data and the surface data such that the tooth in the radiograph data substantially matches with the tooth in the surface data; and calculating a dimension of a portion of the gum tissue associated with the tooth based on the combination of the radiograph data and the surface data. Disclosed herein are more specific examples related to such a method. It will be understood that the more specific examples disclosed herein can also be implemented in systems and/or devices, including those disclosed herein.

As described (e.g., in reference to FIG. 11B), a combination of radiograph data and surface data can be utilized to obtain gum condition information (e.g., gum pocket depth information) at a plurality of locations of a given tooth. For example, such locations can include locations (e.g., six locations) about a given tooth commonly probed in a periodontal probing process, so as to allow the six gum pocket depth measurements to be included in a common format of a patient chart.

Figure 18:
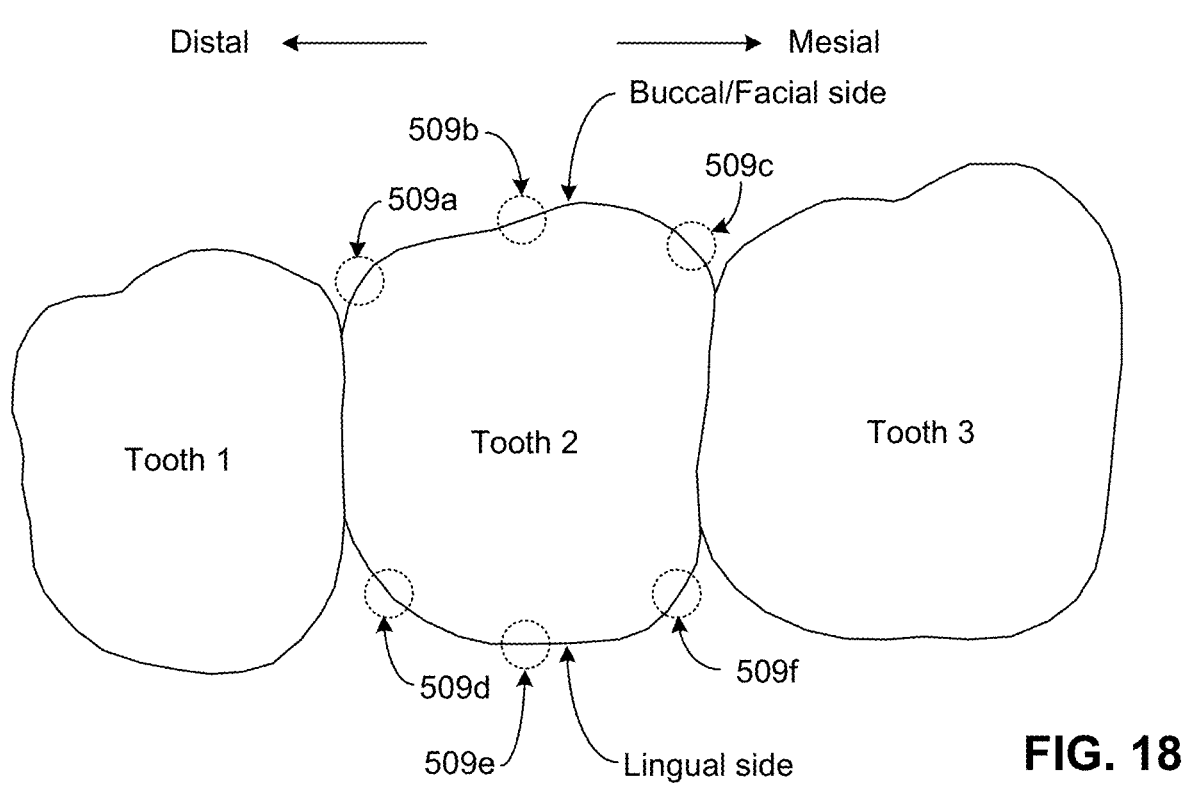
FIG. 18 depicts a tooth where a periodontal probing process may be applied at a number of locations.

FIG. 18 depicts a tooth (e.g., Tooth 2) where six locations 509a-509f corresponding to six locations where a periodontal probing process may be applied, similar to the example of FIG. 11B. In such an example context, FIG. 19 shows that in some embodiments, combined data (also referred to herein as merged data) can include data representative of a sectional view of a combination of radiograph data (CBCT data) and surface data (e.g., intraoral scan data).

Figure 19:
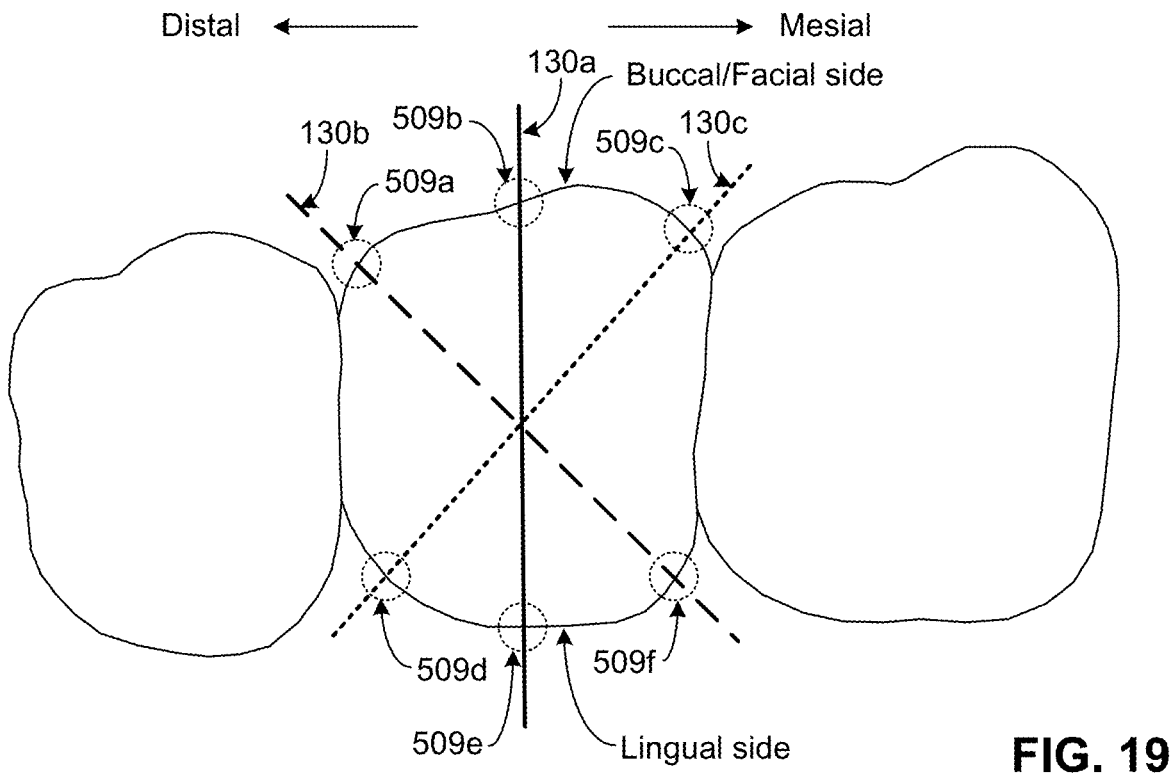
FIG. 19 shows that in some embodiments, combined data can include data representative of a sectional view of a combination of radiograph data and surface data.

For example, and referring to FIG. 19, merged data 130a can include data representative of a plane that includes locations 509b and 509e. Similarly, merged data 130b can include data representative of a plane that includes locations 509a and 509f; and merged data 130c can include data representative of a plane that includes locations 509c and 509d.

It is noted that in the example FIG. 19, in some embodiments, a given merged data plane can include a selected location on the buccal/facial side and a selected location on the lingual side. For example, a merged data plane 130a is shown to include a location 509b on the buccal/facial side and a location 509e on the lingual side.

FIG. 19 also shows that in some embodiments, a merged plane data can include locations on buccal/facial and lingual sides that are at approximately opposing corners of a tooth. For example, a merged data plane 130b is shown to include a location 509a on the buccal/facial side and a location 509f on the lingual side. Similarly, a merged data plane 130c is shown to include a location 509c on the buccal/facial side and a location 509d on the lingual side. In some embodiments, such cross-corner arrangement of a merged data plane can be utilized to provide a sectional view at a given location where the plane intersects a tangent line at the location at an angle that is at, near, or closer to 90 degrees.

Figure 20B:
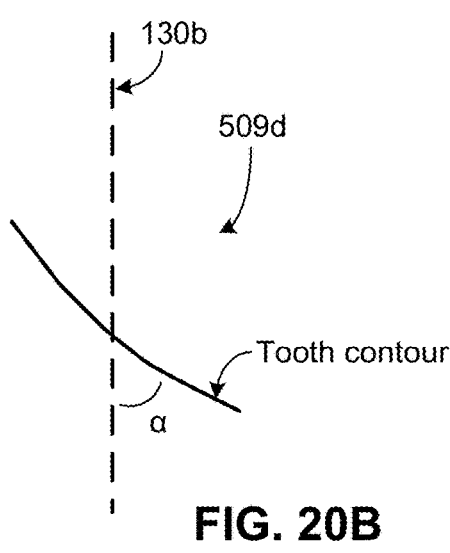
FIG. 20B shows an enlarged view of a region about the indicated location of the example of FIG. 20A.
Figure 20A:
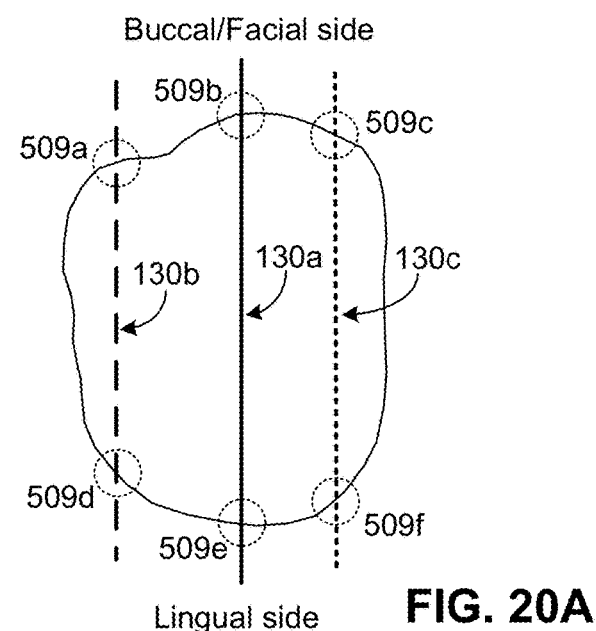
FIG. 20A shows an example where three merged data planes are formed for a given tooth, such that each merged data plane intersects with a tangent line at a location on the buccal/facial side and tangent line at a location on the lingual side.

FIG. 20A shows an example where three merged data planes 130a, 130b, 130c are formed for a given tooth, such that each merged data plane intersects with a tangent line at a location on the buccal/facial side and tangent line at a location on the lingual side, similar to the example of FIG. 19. FIG. 20A is different from FIG. 19, in that in the example of FIG. 20A, there is no cross-corner arrangement of a merged data plane. Thus, in the example of FIG. 20A, a merged data plane 130b is shown to be formed on the distal end (when viewed as in FIG. 19) and includes a location 509a on the buccal/facial side and a location 509d on the lingual side; a merged data plane 130a is shown to be formed at or near a mid-portion and includes a location 509b on the buccal/facial side and a location 509e on the lingual side; and a merged data plane 130c is shown to be formed on the mesial end (when viewed as in FIG. 19) and includes a location 509c on the buccal/facial side and a location 509f on the lingual side.

FIG. 20B shows an enlarged view of a region about the location 509d on the distal-end/lingual-side corner of the example of FIG. 20A. More particularly, such an example corner is shown to include a tooth contour having a tangent line that forms an acute angle α that is significantly less than 90 degrees with respect to the merged data plane 130b; and such an acute angle α may not be desirable for a sectional view.

Figure 21B:
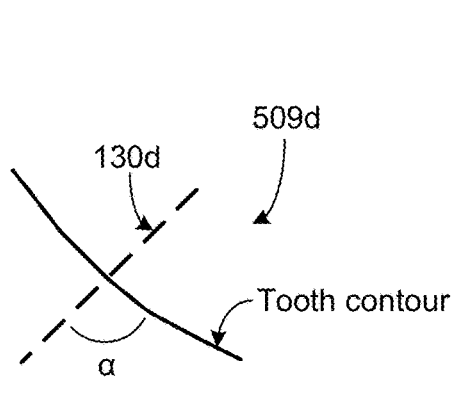
FIG. 21B shows an enlarged view of a region about the indicated location of the example of FIG. 21A.
Figure 21A:
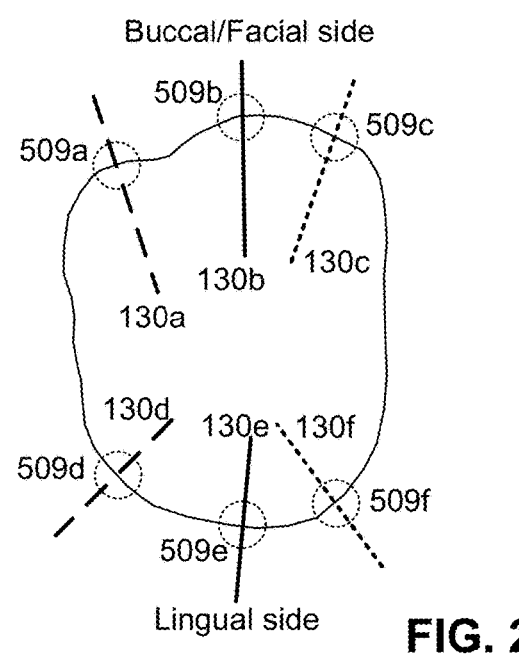
FIG. 21A shows that in some embodiments, a merged data plane as described herein does not necessarily need to include a location on the buccal/facial side of a tooth and a location on the lingual side of the same tooth.

FIG. 21A shows that in some embodiments, a merged data plane as described herein does not necessarily need to include a location on the buccal/facial side of a tooth and a location on the lingual side of the same tooth. Instead, a merged data plane can be formed to include a selected location to provide a desired sectional view, and any other location that may be included in the merged data plane may or may not be utilized.

For example, and referring to FIG. 21A, a merged data plane 130a is shown to be formed to include a location 509a and to intersect with a tangent line at the location 509a at a desired angle. Similarly, each of merged data planes 130b-130f is shown to be formed to include a respect one of locations 509b-509f and to intersect with a respective tangent line at the respective location at a desired angle.

FIG. 21B shows an enlarged view of a region about the location 509d on the distal-end/lingual-side corner of the example of FIG. 21A. More particularly, such an example corner is shown to include a tooth contour having a tangent line that forms an angle α that is or near 90 degrees with respect to the merged data plane 130d.

In some embodiments, a merged data plane can be formed to include a selected location of a tooth, such that the merged data plane forms an angle, relative to a tangent line at the selected location, within a range of 60 degrees to 120 degrees, 70 degrees to 110 degrees, 80 degrees to 100 degrees, or 85 degrees to 95 degrees.

Figures 22, 23:
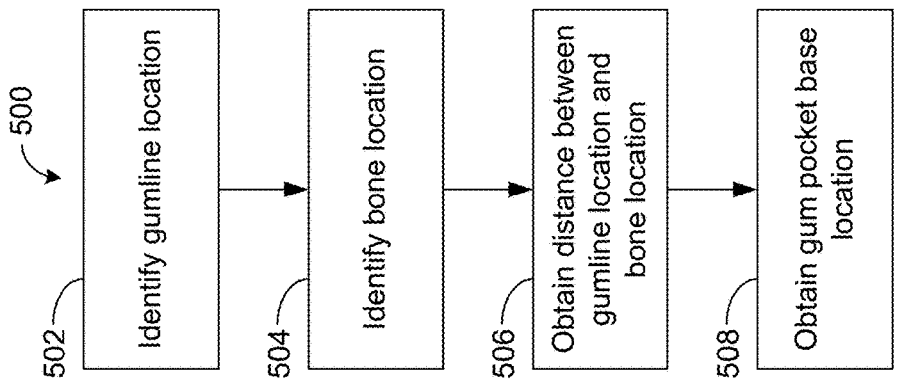
FIG. 22 shows an image representative of a merged data plane of a tooth, and such an image is shown to include data representative of radiograph data and data representative of intraoral scan surface data.
FIG. 23 shows a process that can be implemented to allow characterization of a gum condition, such as a gum pocket base location.
Figure 24:
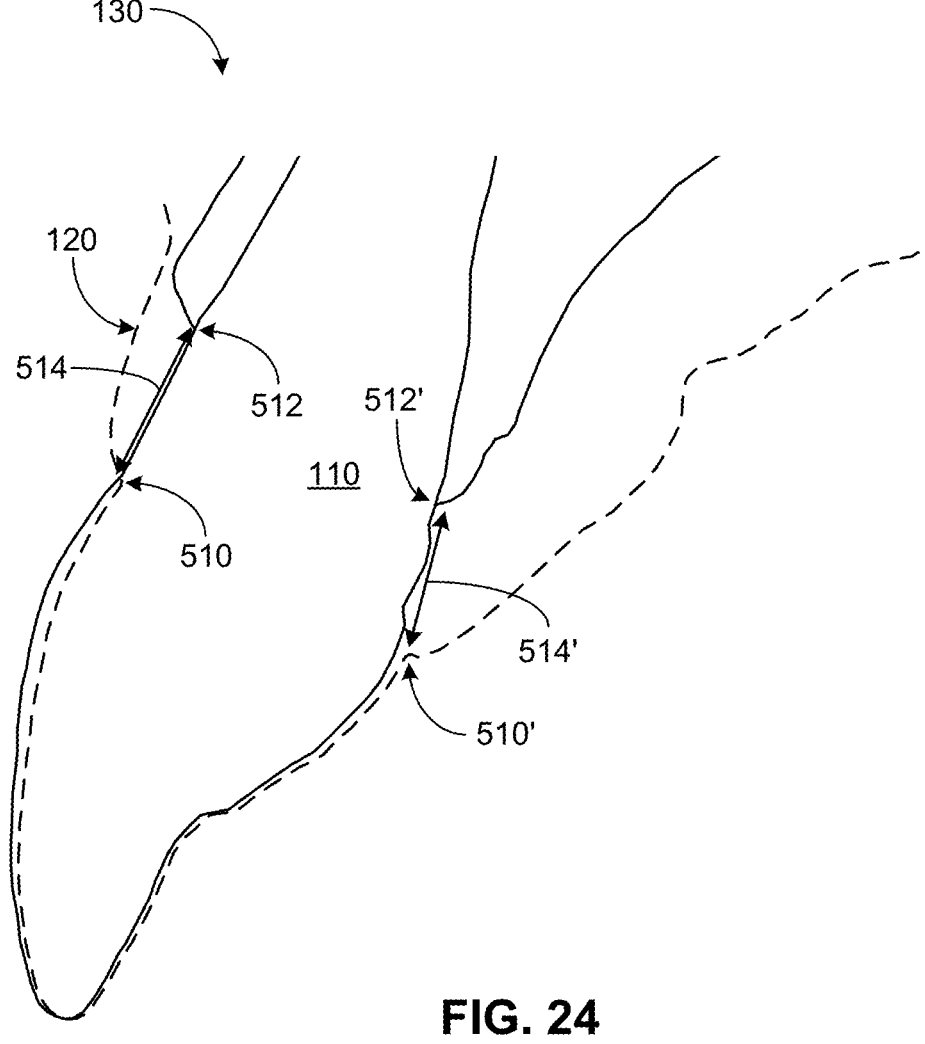
FIG. 24 depicts line traces of various features shown in the image of FIG. 22.

FIG. 22 shows an image representative of a merged data plane 130 of a tooth, and such an image is shown to include data representative of CBCT radiograph data 110 and data representative of intraoral scan surface data 120. FIG. 24 depicts line traces of various features shown in the image of FIG. 22.

Referring to the examples of FIGS. 22 and 24, the merged data plane 130 is shown to include a gumline location 510 and a bone location 512 (e.g., along the top portion 112 of the corresponding bone in FIG. 6A) on the buccal/facial side and a gumline location 510' and a bone location 512' on the lingual side. In some embodiments, such gumline locations and bone locations can be identified, and respective separation distances (514 and 514') between the gumline locations and bone locations can be calculated, as described herein.

It is noted that in the examples of FIGS. 22 and 24, both sets of gumline locations and bone locations on the buccal/facial and lingual sides appear to be sufficiently identifiable as described herein. However, and as described herein in reference to FIGS. 18 to 21, it will be understood that identification of both sets of gumline locations and bone locations on the buccal/facial and lingual sides may or may not be implemented. For example, if a merged data plane provides clear identification of gumline and bone locations on one side of a tooth, but not on the other side of the tooth, another merged data plane can be generated to obtain a clear identification of gumline and bone locations on the other side of the tooth.

FIG. 23 shows a process 500 that can be implemented to allow characterization of a gum condition, such as a gum pocket base location. As examples for various process blocks of the process 500, the buccal/facial side is referenced in the merged data plane 130 of FIGS. 22 and 24. However, it will be understood that a similar process can be implemented for the lingual side in the merged data plane 130.

Referring to FIG. 23, in process block 502, a gumline location can be identified in a merged data plane. For the purpose of description, it will be understood that such a merged data plane can be generated approximately contemporaneously as the process 500, or have been generated prior to the process 500. It will also be understood that such a merged data plane may or may not have a visual representation such as an image (e.g., as in FIG. 22). In the example merged data plane 130 of FIGS. 22 and 24, such a gumline location is indicated as 510. Examples of how such a gumline location can be determined are described herein in greater detail.

In process block 504, a bone location can be identified in the merged data plane. In the example merged data plane 130 of FIGS. 22 and 24, such a bone location is indicated as 512. Examples of how such a bone location can be determined are described herein in greater detail.

In process block 506, a distance between the gumline location and the bone location can be calculated. In the example merged data plane 130 of FIGS. 22 and 24, such a distance is indicated as 514. In some embodiments, the distance 514 can be a length of a straight line between the two locations 510, 512. In some embodiments, the distance 514 can be based on a contour of the tooth (e.g., a path integral length) in the merged data plane 130 between the two locations 510, 512.

In process block 508, a gum pocket base location can be calculated based on the distance obtained in the process block 506. In some embodiments, and as described herein, such a gum pocket base location can be estimated by subtracting a biologic width value (e.g., approximately 2 mm) from the distance (514 in FIGS. 22 and 24).

FIGS. 25 to 29 show non-limiting examples of how gumline and bone locations can be obtained from a merged data plane. Such examples are described in the context of the merged data plane 130 of FIGS. 22 and 24; however, it will be understood that one or more features of location-determination as described herein can also be implemented in other merged data planes.

Figure 25:
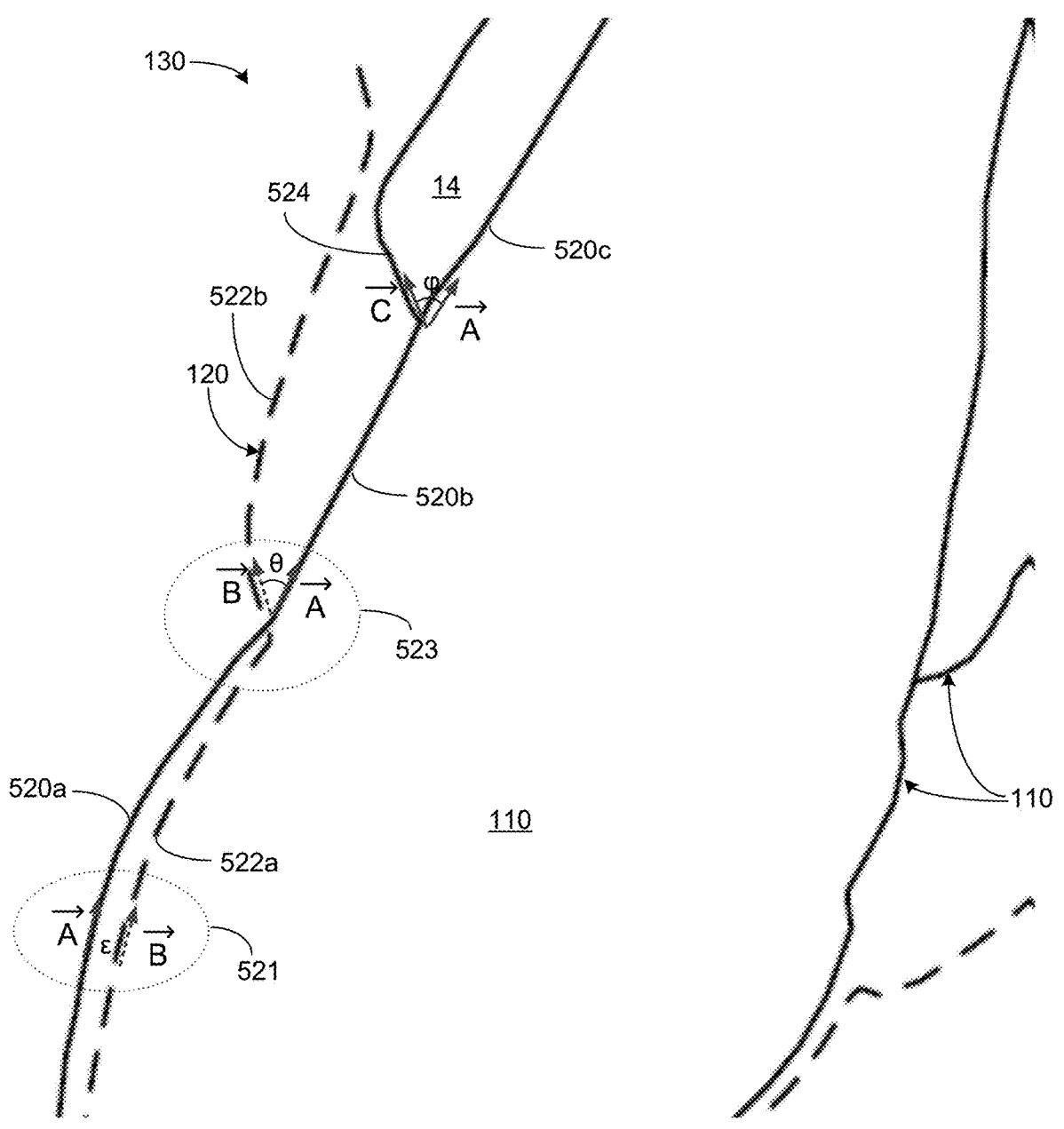
FIG. 25 depicts an enlarged view of the example merged data plane of FIGS. 22 and 24 for clarity.

FIG. 25 depicts an enlarged view of the example merged data plane 130 of FIGS. 22 and 24 for clarity. In FIG. 25, the CBCT radiograph data 110 is shown to include a portion 520a corresponding to an exposed portion of the tooth, and a portion 520b corresponding to a portion covered by the gum. The intraoral scan surface data 120 is shown to include a portion 522a corresponding to the exposed portion of the tooth, and a portion 522b corresponding to a portion of the gum covering the covered portion 520b of the tooth.

Referring to FIG. 25, it is noted that the portion 520a of the CBCT radiograph data 110 and the portion 522a of the intraoral scan surface data 120 correspond to the same exposed portion of the tooth. Thus, in an ideally merged data plane, such two portions (520a and 522b) would overlap substantially completely with each other. However, there may be errors (e.g., merging errors) that result in the two portions (520a and 522b) not matching ideally. For example, in FIG. 25, the two portions (520a and 522b) are shown to be separated by as much as quantity E. In some embodiments, such an error can be negligible, and/or be safely ignored, when compared to a distance being measured, such as the distance between the gumline location (510 in FIG. 24) and the bone location (512). In some embodiments, the separation quantity & may also be negligible, and/or be safely ignored, when compared to a smaller dimension such as a gum pocket depth dimension.

FIG. 25 shows that in some embodiments, the portion 520a of the CBCT radiograph data 110 and the portion 522a of the intraoral scan surface data 120 can be traced by pluralities of respective two-dimensional vectors from a common (or approximately common) starting location. Such a starting point can be, for example, the tip of the tooth or anywhere along the exposed portion of the tooth. For the latter example, suppose that an average length of an exposed tooth is L. Then, a starting location can be, for example, L/2 towards the gum. Such a starting location away from the tip of the tooth can allow reduction in, for example, computing time being utilized for the foregoing vector tracing from the starting location to an as-yet-unknown gumline location.

Referring to FIG. 25, the portion 520a of the CBCT radiograph data 110 can be traced by a series of two-dimensional vectors A, from the starting location. Similarly, the portion 522a of the intraoral scan surface data 120 can be traced by a series of two-dimensional vectors B, from the starting location. In some embodiments, the tracings of the portion 520a and the portion 522a can include the same number of two-dimensional vectors A and B. Such vectors A and B may have a constant magnitude, varying magnitudes, or some combination thereof, depending on curvatures of the respective contours.

In some embodiments, the two-dimensional vectors A and B that trace the respective portions (520a and 522a) can be utilized to obtain an opening angle θ between for a pair of corresponding vectors A and B. For example, and referring to FIG. 25, vectors A and B are depicted at a region 521 that is away from a region 523 that includes the gumline location. In the region 521, the two vectors A and B have generally the same direction, whether or not they are separated (e.g., by quantity ε). Thus, in some embodiments, a vector operation such as a dot product operation can be performed with the vectors A and B as shown in Equation 1.

$$A \cdot B = \vec{A} \cdot \vec{B} = A_x B_x + A_y B_y = \|\vec{A}\| \, \|\vec{B}\| \cos\theta \qquad (1)$$

For the purpose of Equation 1, it is assumed that the merged data plane 130 of FIG. 25 can be represented by a local X-Y plane. Configured in such a manner, $A_x B_x + A_y B_y$ and $\|\vec{A}\| \|\vec{B}\|$ can be calculated, thereby allowing the opening angle θ to be calculated as $$\theta = \cos^{-1}\left( \frac{A_x B_x + A_y B_y}{\|\vec{A}\| \, \|\vec{B}\|} \right). \qquad (2)$$

It is noted that since the portions (520a and 522a) ideally form the same curve, the opening angle θ among two corresponding vectors A and B along the curve can be expected to be close to or equal to zero, until a divergence occurs due to the presence of a gumline location in the region 523.

Referring to FIG. 25, in the region 523, the two vectors A and B are shown to diverge from each other due to the presence of the gum, beginning at the gumline location. The opening angle θ of such diverging vectors A and B can be calculated based on Equation 2.

In some embodiments, an opening angle θ between two corresponding vectors A and B being greater than a threshold value can provide an indication of presence of a gumline location. In some embodiments, such a gumline location can be at, for example, a common tail location of the two corresponding vectors A and B. If the two corresponding vectors A and B are displaced relative to each other, one of the two corresponding vectors A and B can be shifted to the other vector to provide a common tail location.

In some embodiments, the foregoing threshold value of the opening angle θ can be, for example, 10 degrees, 15, degrees, 20 degrees, 25 degrees, 30 degrees, 35 degrees, 40 degrees or 45 degrees.

As described herein, the example method of calculating opening angles between corresponding pairs of A and B along the portions 520a and 522a by Equation 2 can be relatively insensitive to one vector being displaced relative to the other vector, even if the CBCT radiograph data 110 and the intraoral scan surface data 120 do not provide an ideal merged data plane 130.

It is noted that in some embodiments, tracing of the portions 520a and 522a as described herein can be utilized to fine tune the merging of the of the CBCT radiograph data 110 and the intraoral scan surface data 120. For example, a series of local values of separation quantity ε can be obtained for the pairs of corresponding vectors A and B along the portions 520a and 522a. With an understanding that such portions (520a and 522a) are of the same feature of the tooth, one of the CBCT radiograph data 110 and the intraoral scan surface data 120 can be shifted, rotated, and/or otherwise adjusted to better match with the other data. In some embodiments, obtaining of a gumline location can be repeated with the fine tuned merging of the CBCT radiograph data 110 and the intraoral scan surface data 120.

In the example of FIG. 25, the CBCT radiograph data 110 is shown to include a portion 520b between the now-calculated gumline location (510 in FIG. 24) and yet-to-be found bone location (512 in FIG. 24). In some embodiments, such a bone location can be found by one or more methods. For example, the portion 520b can be traced from the gumline location until a junction is found, where the portion 520b continues as a root portion 520c from the junction, and a bone portion 524 diverges away from the root portion 520c. In some embodiments, the presence of such a junction can provide the location of the same.

In some embodiments, at such a junction, a vector A along the beginning portion of the root portion 520c and a vector C along the beginning portion of the bone portion can be obtained, and an opening angle φ can be calculated (e.g., as described herein in reference to Equations 1 and 2). In some embodiments, an opening angle q between two vectors A and C being greater than a threshold value can provide an indication of, and/or confirmation of, presence of a bone location. In some embodiments, such a bone location can be at, for example, a common tail location of the two vectors A and C.

In some embodiments, the foregoing threshold value of the opening angle φ can be, for example, 10 degrees, 15, degrees, 20 degrees, 25 degrees, 30 degrees, 35 degrees, 40 degrees or 45 degrees.

In some embodiments, the root portion 520c of FIG. 25 can be identified by, for example, a dark line representative of gum tissue between the root and bone structures. It is noted that in some merged data planes, such a feature corresponding to gum tissue may not show sufficiently clearly to form an appropriate line.

In some embodiments, if such a root portion (520c in FIG. 25) is not sufficiently clear, a bone location (512 in FIG. 24) can be found in an alternate manner. For example, and referring to FIG. 25, the portion 520b can be traced by a series of vectors A, and a deviation from an expected direction of such a vector can be indicative of presence of a bone location.

For example, suppose that a first vector A begins at the gumline location so as to be approximately along a first segment of the portion 520b. A second vector A can then continue from the head of the first vector A so as to be approximately along a next segment of the portion 520b. A dot product of the first and second vectors A can be calculated to obtain an opening angle as described herein; and if such an opening angle is greater than a threshold value (e.g., 10 degrees, 15, degrees, 20 degrees, 25 degrees, 30 degrees, 35 degrees, 40 degrees or 45 degrees), then the tail of the latest vector A can be considered to be approximately at the bone location. In some embodiments, an additional condition can be applied, where the latest vector diverges away outward from the root portion 520c.

In the example of FIG. 25, the vector indicated as C can be the latest vector A in the foregoing example technique. Accordingly, the vector C is shown to be diverging away from the previous vector A at an opening angle φ, and the tail of the vector C can be considered to be approximately the bone location (512 in FIG. 24).

FIG. 26 shows a process 530 that can be implemented to calculate a gumline location in a merged data plane, such as the example merged data plane 130 of FIG. 25. In process block 531, a first tooth contour segment can be obtained from a radiograph data portion of the merged data plane, and a corresponding second tooth contour segment can be obtained from a surface image portion of the merged data plane. In some embodiments, such first and second contour segments can be represented as two-dimensional vectors.

In process block 532, the first tooth contour segment and the second tooth contour segment can be compared to obtain an opening angle θ. In some embodiments, such comparison can include comparing of two vectors representative of the two contour segments. In some embodiments, such a comparison of the two vectors can include a dot product of the two vectors to obtain the opening angle θ.

In a decision block 533, the process 530 can determine whether the opening angle θ is greater than a threshold angle $\theta_{max}$. If the answer is No, the process 530 can determine the next set of first and second contour segments in process block 536 and repeat process block 531. In the answer is Yes, the process 530 can determine whether the second tooth contour segment is angled away from the tooth in a decision block 534. If the answer is No, the process 530 can determine the next set of first and second contour segments in process block 536 and repeat process block 531. If the answer is Yes, the process 530 in process block 535 can designate a location associated with the first and second tooth contour segments as a gumline location.

Figure 27:
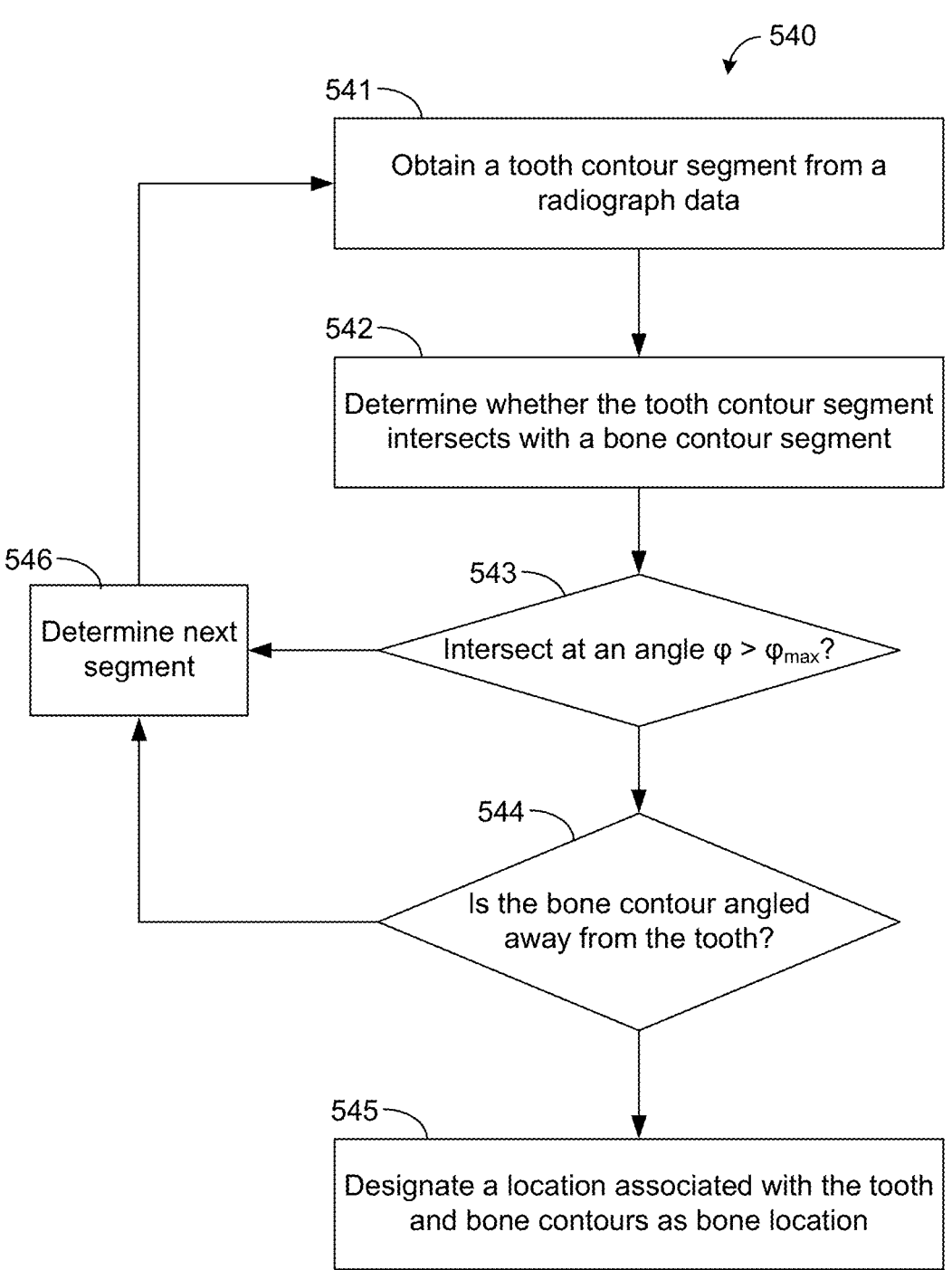
FIG. 27 shows a process that can be implemented to calculate a bone location in a merged data plane, such as the example merged data plane of FIG. 25.

FIG. 27 shows a process 540 that can be implemented to calculate a bone location in a merged data plane, such as the example merged data plane 130 of FIG. 25. In process block 541, a tooth contour segment can be obtained from a radiograph data portion of the merged data plane.

In process block 542, the process 540 can determine whether the tooth contour segment intersects with a bone contour segment at an opening angle φ. Examples of such intersection determination are described above in reference to FIG. 25.

In a decision block 543, the process 540 can determine whether the opening angle φ is greater than a threshold angle $\varphi_{max}$. If the answer is No, the process 540 can determine the next contour segment in process block 546 and repeat process block 541. In the answer is Yes, the process 540 can determine whether the bone contour segment is angled away from the tooth in a decision block 544. If the answer is No, the process 540 can determine the next contour segment in process block 546 and repeat process block 541. If the answer is Yes, the process 540 in process block 545 can designate a location associated with the tooth contour segment and bone contour segment as a bone location.

In some embodiments, one or more features of the present disclosure can be implemented utilizing pattern recognition algorithm(s), with or without artificial intelligence (AI) functionality. For example, FIG. 28 depicts an isolated view of a portion 550 of the merged data plane 130 of FIG. 25, and FIG. 29 shows a process 570 that can be implemented to find selected patterns in a merged data plane such as the merged data plane 550 of FIG. 28.

Figure 28:
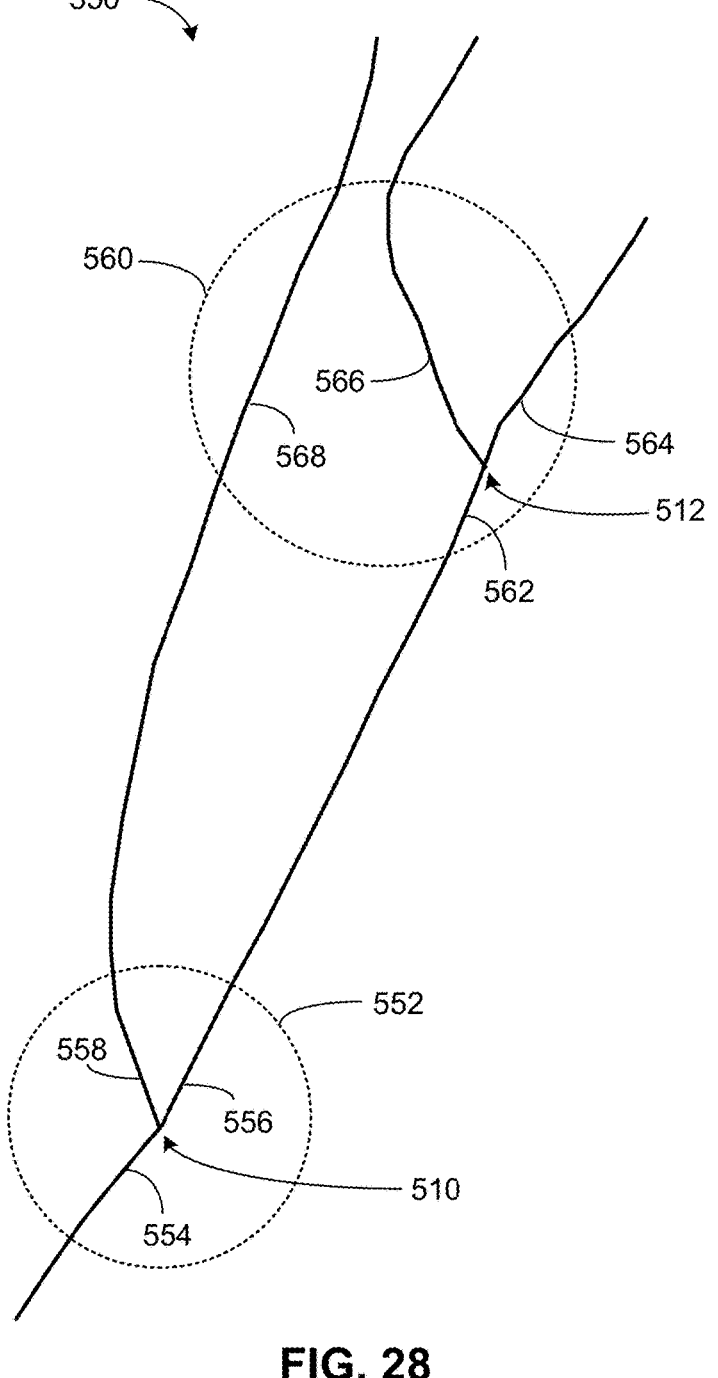
FIG. 28 depicts an isolated view of a portion of the merged data plane of FIG. 25.
Figure 29:
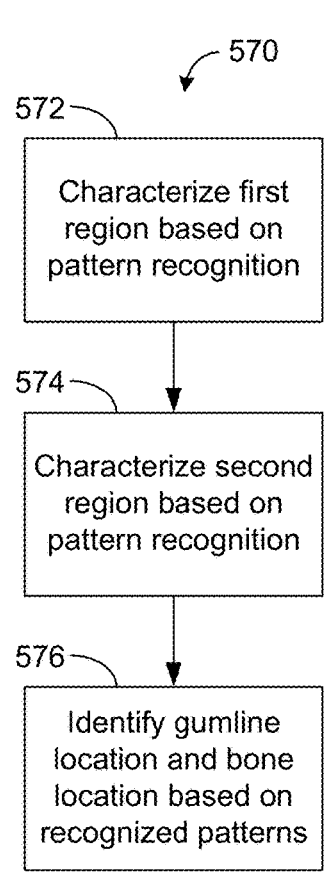
FIG. 29 shows a process that can be implemented to find selected patterns in a merged data plane such as the merged data plane of FIG. 28.

Referring to FIGS. 28 and 29, the process 570 can include process block 572 where a first region can be characterized based on pattern recognition. In FIG. 28, such a first region can be a region indicated as 552 and including a gumline location 510. By way of an example, a pattern that includes an overlapped portion 554 (having both a CBCT radiograph data portion and an intraoral scan surface data portion) branching into an intraoral scan surface data-only portion 558 and a CBCT radiograph data-only portion 556 can be searched for and obtained. In such an obtained pattern, the branching location can be considered to be the gumline location 510.

The process 570 can further include process block 574 where a second region can be characterized based on pattern recognition. In FIG. 28, such a second region can be a region indicated as 560 and including a bone location 512. By way of an example, a pattern that includes a CBCT radiograph data-only portion 562 intersecting with another CBCT radiograph data-only portion 566, and an intraoral scan surface data-only portion 568 that does not overlap or intersect with the portions 562 and 566 can be searched for and obtained. In such an obtained pattern, the intersecting location can be considered to be the bone location 512. In some embodiments, an additional feature or segment 564 (from the CBCT radiograph data) extending from the intersecting location can also be utilized.

The process 570 can further include process block 576 where gumline location and bone location are identified based on the recognized patterns associated with the first and second regions.

Figure 30:
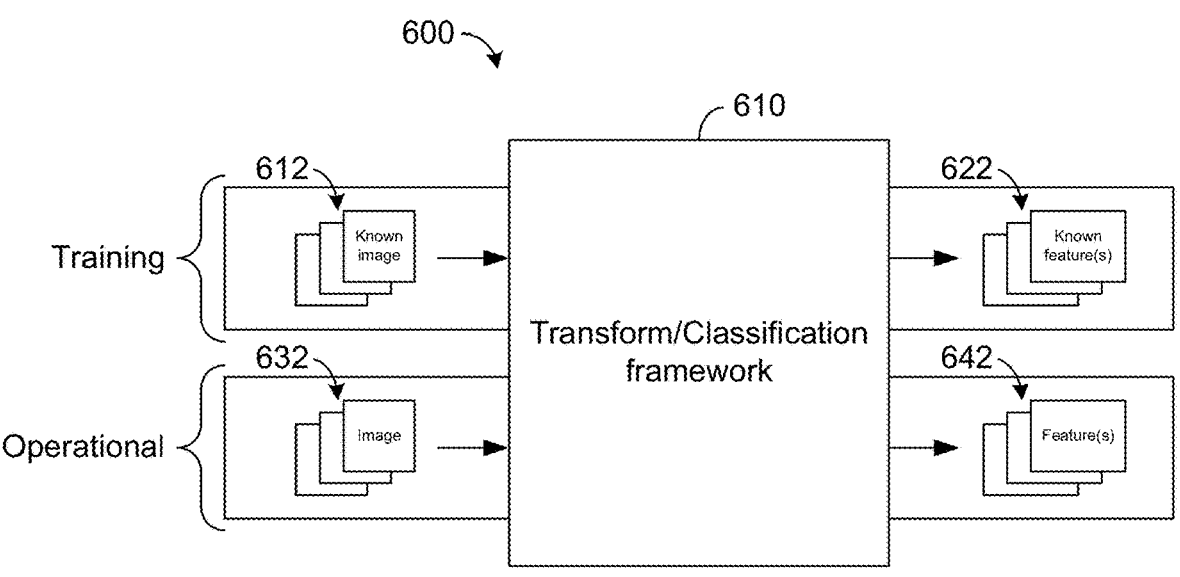
FIG. 30 shows an example of an architecture that can be implemented for identifying one or more periodontal features described herein.
Figure 31:
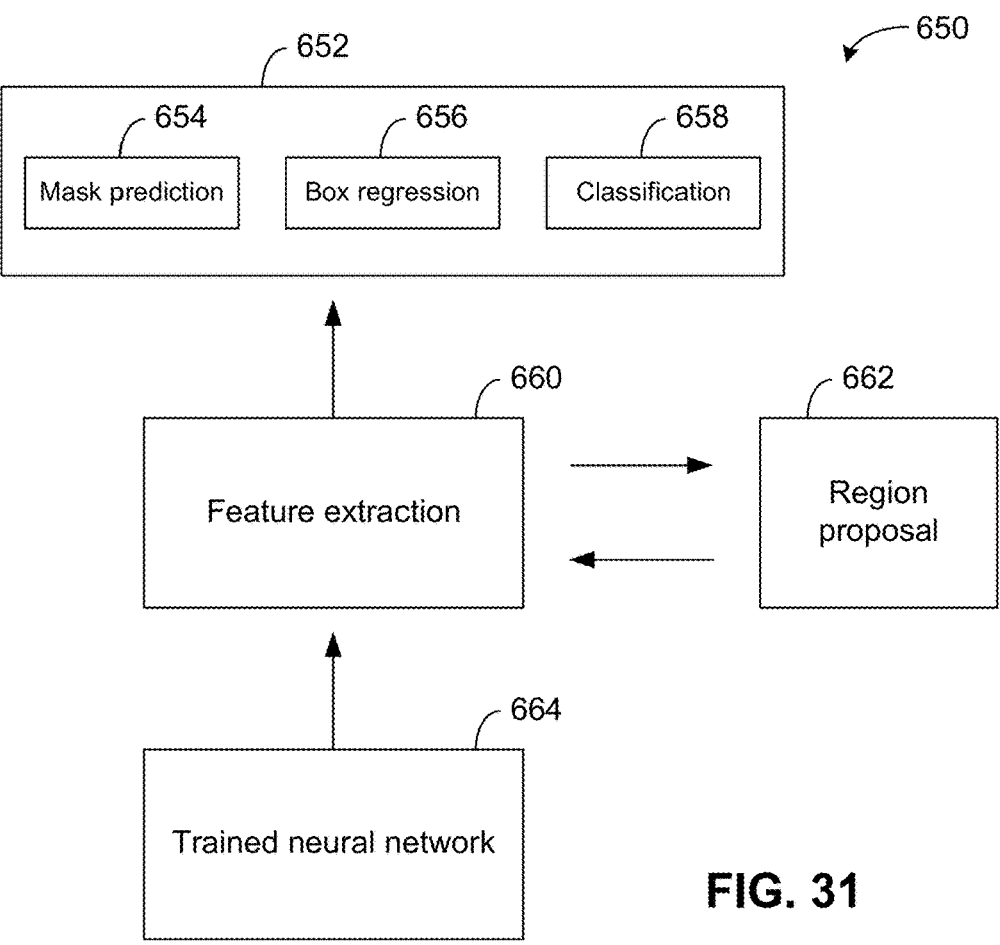
FIG. 31 depicts an example neural network feature-classification/identification framework that can be utilized to identify one or more periodontal features described herein.

FIGS. 30 and 31 show examples of processes having some or all of artificial intelligence (AI), machine learning and neural network functionalities that can be utilized for the examples of FIGS. 28 and 29.

FIG. 30 shows an example of an architecture 600 that can be implemented for identifying one or more periodontal features described herein. In some embodiments, such an architecture can be implemented in and/or be associated with a control circuitry and include one or more processors, data storage devices, connectivity features, substrates, passive and/or active hardware circuit devices, chips/dies, and/ or the like. For example, the architecture 600 may employ machine learning functionality to perform automatic periodontal feature detection on, for example, slice-images obtained from merged data as described herein.

In some embodiments, the architecture 600 of FIG. 30 can be configured to operate on image-type data structures, such as slice-images representing respective sectional views of a three-dimensional representation of the merged data. Such input data can be processed by a transform framework 610 associated with an image processing portion of the architecture 600. In some embodiments, the transform framework 610 can include suitable or desirable transform and/or classification architecture, such as suitable or desirable artificial neural network architecture.

In some embodiments, transform framework 610 can be trained with a number of known slice-images 612 and target labels 622 corresponding to the respective slice-images 612 as input/output pairs. The transform framework can be configured to adjust one or more parameters or weights associated therewith to correlate the known input and output image data. For example, the transform framework 610 can include neural network functionality and be trained using a labelled dataset and/or machine learning. In some embodiments, the machine learning functionality can be configured to execute the learning/training in any suitable or desirable manner.

In some embodiments, the known target label 622 can be generated at least in part by manually labeling known features in the known slice-images 612. For example, manual labels can be determined and/or applied by an appropriately trained person to identify a plane showing a sectional view of a set of teeth (e.g., as in FIG. 18) and intersection locations of merged data planes for each tooth, as well as identification of features such as gumline and bone locations (e.g., 510 and 512 in FIGS. 22 to 24) in each merged data plane (slice-image). In some embodiments, the known input/output pairs can provide at least some of the foregoing parameter(s) of the transform framework 610, which may or may not be dynamically updatable.

In some embodiments, the known target labels 622 can include a boundary and/or a notable area associated with the known features therein. The architecture 600 can be configured to generate operational target labels 642 to indicate whether a particular image of operational slice-images 632 includes a target feature or not, such that further processing can be performed on the images that are identified as containing one or more of the target features to further identify such target feature(s).

In some embodiments, the architecture 600 can be further configured to generate operational target labels 642 associated with operational slice-images 632 using the trained version of the transform framework 610. For example, during or after merged data is obtained for a patient, operational slice-images 632 of the teeth of the patient can be processed using the transform framework 610 to generate operational target labels 642 identifying the presence and/or position of one or more target features in the operational images 632. For example, in some embodiments, slice-images 632 can be processed by the transform framework 610 to identify the presence and/or position of a target gumline and bone features as described herein.

In some embodiments, the transform framework 610 can be configured to identify the target feature(s), as well as other features and/or regions associated with the target feature(s). The transform framework 610 can include an artificial neural network, such as a convolutional neural network. For example, the transform framework 610 can include or have capability to implement a deep learning architecture that takes in an input image, assigns learnable weights/biases to various aspects/objects in the image to differentiate one from another. In some embodiments, filters/characteristics of the transform framework 610 can be hand-engineered or may be learned through machine learning.

In some embodiments, the transform framework 610 can include a plurality of neurons (e.g., layers of neurons) corresponding to overlapping regions of an input image that cover the visual area of the input image. The transform framework 610 can further be configured to operate to flatten the input image, or portion(s) thereof, in some manner. The transform framework 610 can be configured to capture spatial and/or temporal dependencies in the input images 632 through application of filters. Such filters can be executed in various convolution operations to achieve a desired output data. Such convolution operations may be used to extract features, such as edges, contours, and the like. The transform framework 610 can include any number of convolutional layers, where more layers can provide for identification of higher-level features.

In some embodiments, the transform framework 610 can further include one or more pooling layers, which can be configured to reduce the spatial size of convolved features, which may be useful for extracting features which are rotational and/or positional invariant, as with some features. Once prepared through flattening, pooling, and/or other processes, the image data can be processed by a multi-level perceptron and/or a feed-forward neural network. Furthermore, backpropagation can be applied to each iteration of training. The transform framework can be configured to be able to distinguish between dominating and low-level features in the input images and classify them using any suitable or desirable technique.

FIG. 31 depicts an example neural network feature-classification/identification framework 650 that can be utilized to identify one or more periodontal features described herein. In some embodiments, the framework 650 can include, for example, a convolutional neural network architecture and may include one or more of the shown components, which may represent respective functional components each of which may be embodied in one or more portions or components of control circuitry associated with any of the systems, devices, and/or methods of the present disclosure. The framework 650 can represent an embodiment of the transform circuitry 610 of FIG. 30 or a portion thereof.

In the example of FIG. 31, the neural network framework 650 can include a pre-trained neural network 664, and a feature-extraction component 660 such as a feature pyramid network. The feature extraction component 660 can be configured to extract one or more feature maps of an input image and/or engineer feature-detector contours. In embodiments implementing feature pyramid network functionality, multiple images may be processed with different levels of resolution to provide output variants.

In the example of FIG. 31, the neural network framework 650 can further include a region proposal network component 662. Such a region proposal network can be configured to propose certain bounding boxes on an image that encapsulate targets indicated/identified on feature maps generated and/or provided by the feature extraction component 660.

In some embodiments, a coarse-to-fine processing diagram can be executed to extract a target in an image. Proposed bounding boxes provided by the region proposal network 662 can be utilized by one or more additional components collectively indicated as 652. For example, a binary classification network component 658 can be configured to classify bounding boxes based on whether or not they contain the target feature of interest. In another example, a box regression network 656 can be implemented and configured to refine boundary boxes proposed by the region proposal network 662. In yet another example, a mask prediction network component 654 can be configured to calculate and/or represent the silhouette or shape/form of identified target feature(s).

Figure 32:
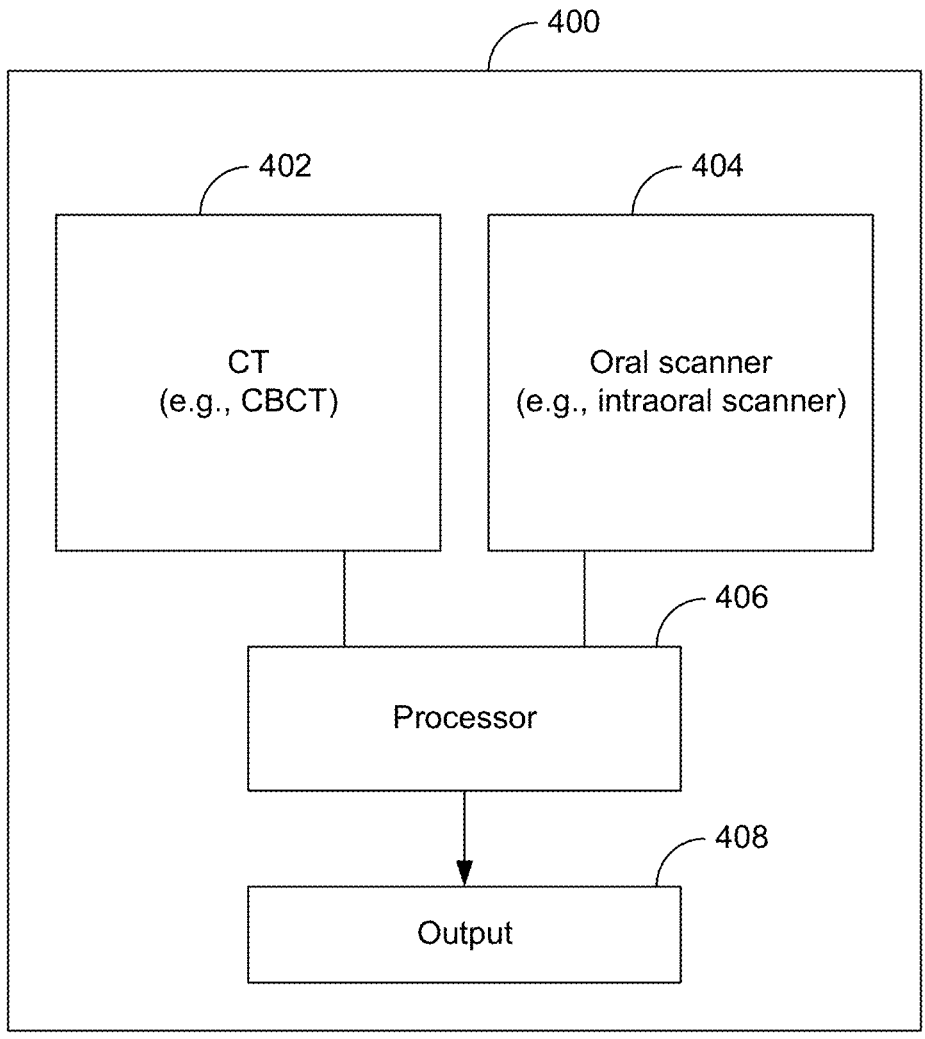
FIG. 32 shows that in some embodiments, a system can be implemented to provide one or more features as described herein.

FIG. 32 shows that in some embodiments, a system 400 can be implemented to provide one or more features as described herein. Such a system can include a computed tomography (CT) apparatus 402 such as a cone beam computed tomography (CBCT) apparatus configured to generate a radiograph and/or related data such as a CBCT radiograph. The system 400 can further include an oral scanner 404 such as an intraoral scanner configured to generate surface data. The system 100 can further include a processor 406 configured to combine outputs of the CT apparatus 402 and the oral scanner 404 and generate an output 408 as described herein.

Figure 33:
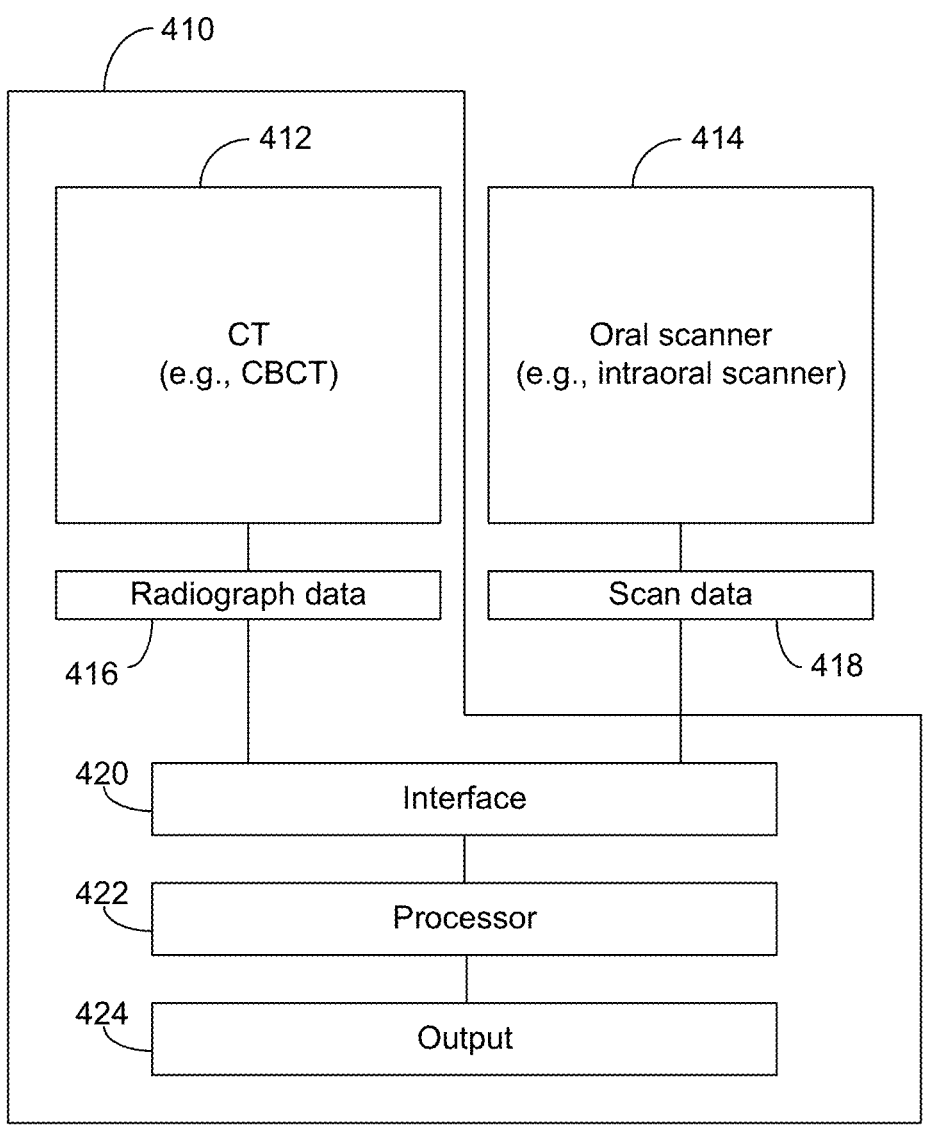
FIG. 33 shows that in some embodiments, a system can be implemented to provide one or more features as described herein; and such a system can include a computed tomography (CT) apparatus such as a cone beam computed tomography (CBCT) apparatus configured to generate a radiograph and/or related data such as a CBCT radiograph, and an interface configured to receive the radiograph data as well as scan data from an oral scanner, such as an intraoral scanner, that is not part of the system.
Figure 34:
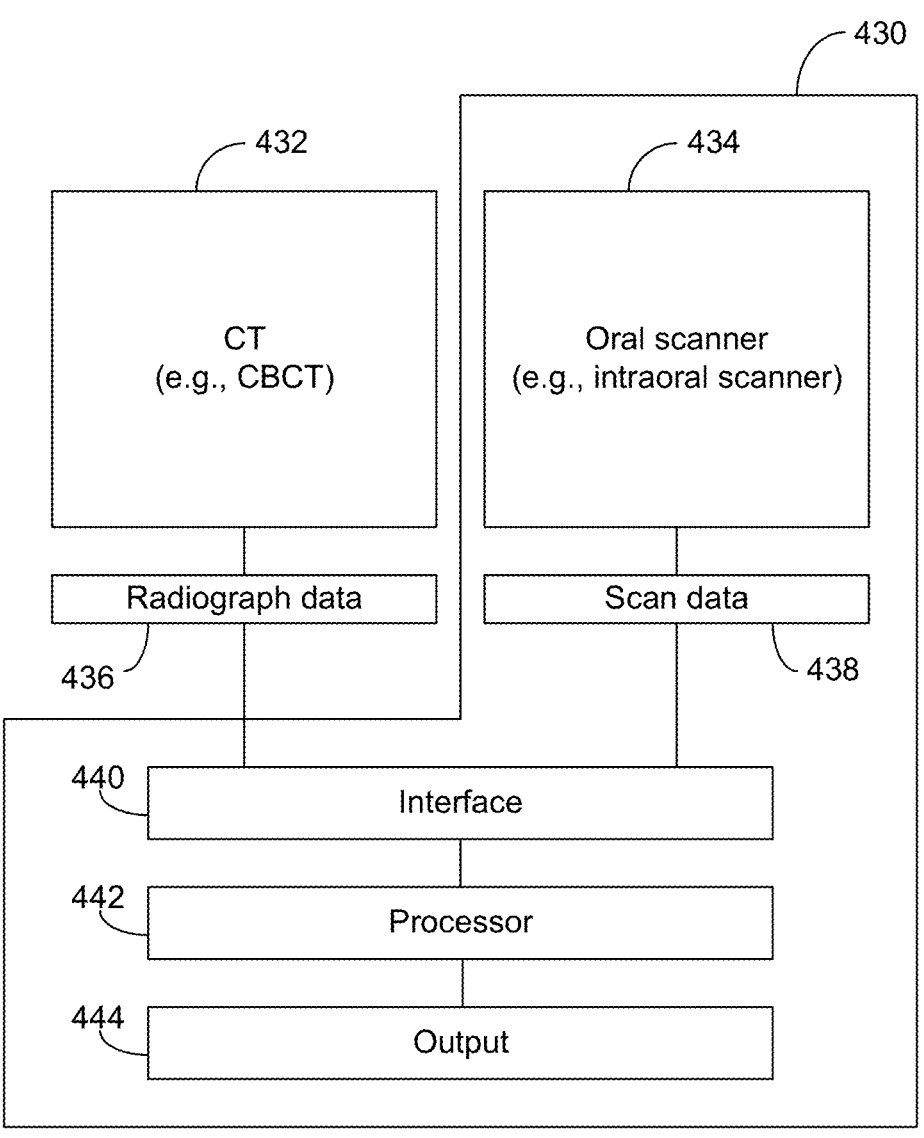
FIG. 34 shows that in some embodiments, a system can be implemented to provide one or more features as described herein; and such a system can include an oral scanner, such as an intraoral scanner, configured to generate scan data, and an interface configured to receive the scan data as well as a radiograph and/or related data, such as a CBCT radiograph, from a CBCT apparatus that is not part of the system.

It is noted that the example of FIG. 32 can be considered to be an integrated system where the system 400 includes both of the CT apparatus 402 and the oral scanner 404. FIGS. 33 and 34 show examples of systems that do not necessarily include both of such components.

For example, FIG. 33 shows that in some embodiments, a system 410 can be implemented to provide one or more features as described herein. Such a system can include a computed tomography (CT) apparatus 412 such as a cone beam computed tomography (CBCT) apparatus configured to generate a radiograph and/or related data 416 such as a CBCT radiograph. The system 410 can further include an interface 420 configured to receive the radiograph data 416 as well as scan data 418 from an oral scanner 414, such as an intraoral scanner, that is not part of the system 410. The system 410 can further include a processor 420 configured to combine the radiograph data 416 and the scan data 418 and generate an output 424 as described herein.

In another example, FIG. 34 shows that in some embodiments, a system 430 can be implemented to provide one or more features as described herein. Such a system can include an oral scanner 434, such as an intraoral scanner, configured to generate scan data 438. The system 430 can further include an interface 440 configured to receive the scan data 438 as well as a radiograph and/or related data 436, such as a CBCT radiograph, from a computed tomography (CT) apparatus 412, such as a cone beam computed tomography (CBCT) apparatus, that is not part of the system 430. The system 430 can further include a processor 442 configured to combine the radiograph data 436 and the scan data 438 and generate an output 434 as described herein.

Figure 35:
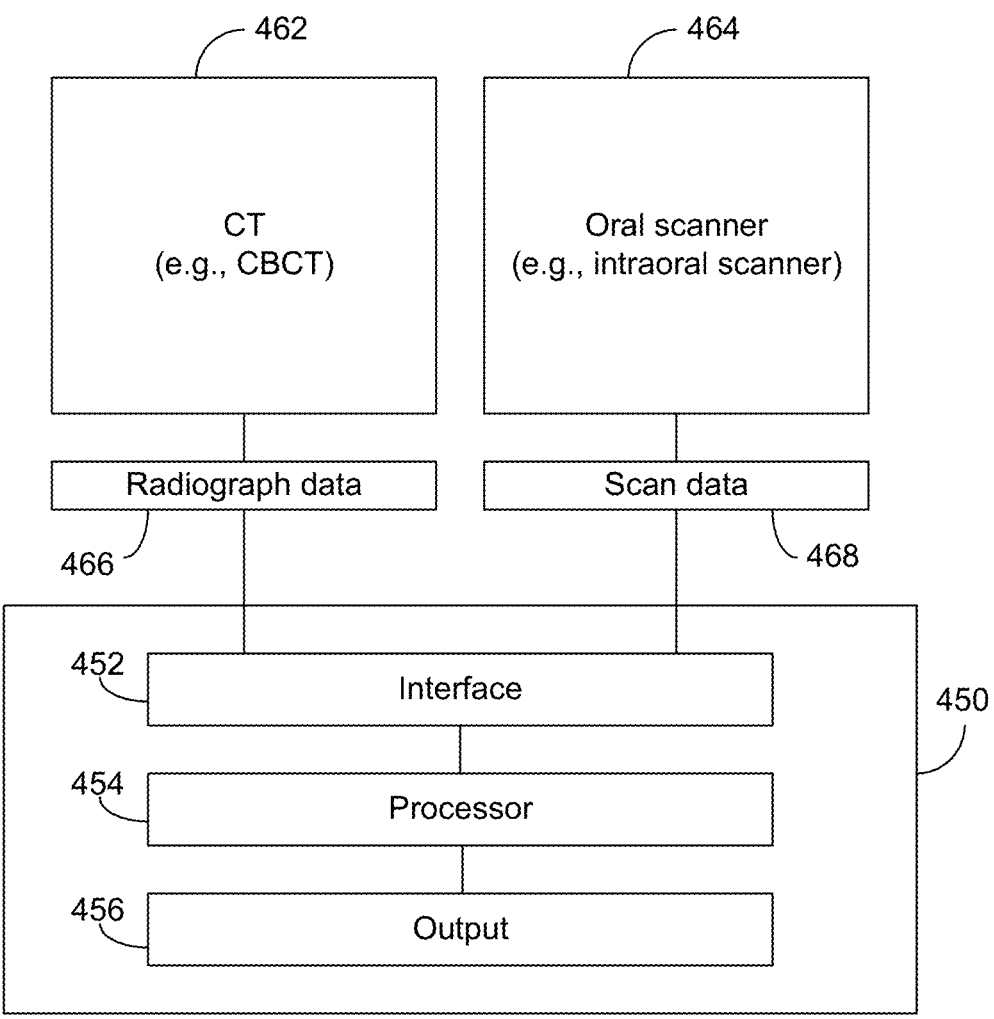
FIG. 35 shows that in some embodiments, a system can be implemented to provide one or more features as described herein, where neither of CT apparatus nor oral scanner is necessarily included in the system.

FIG. 35 shows that in some embodiments, a system 450 can be implemented to provide one or more features as described herein, where neither of CT apparatus 462 nor oral scanner 464 is necessarily included in the system 450. Such a system can include an interface 452 configured to receive radiograph and/or related data 466 generated by the CT apparatus 462 (e.g., CBCT apparatus) that is not part of the system 450, and scan data 468 generated by the oral scanner 464 (e.g., intraoral scanner) that is not part of the system 450. The system 450 can further include a processor 454 configured to combine the radiograph data 466 and the scan data 468 and generate an output 456 as described herein.

It is noted that in various examples described herein, dimensions are utilized to characterize, for example, pocket depth (e.g., d2 in FIGS. 7A to 7C), biologic width (e.g., d1 in FIGS. 7A to 7C), gumline-to-bone feature distance (e.g., 132a, 132b, 132c in FIGS. 7A to 7C), recession (e.g., 133 in FIG. 13C), clinical attachment level (e.g., distance between CEJ and pocket base in FIG. 14), and/or gum thickness (e.g., 135 in FIG. 15). It is also noted that one or more features of the present disclosure can allow characterization of various parts associated with a tooth in 3-dimensional representation. Thus, it will be understood that a dimension as described herein can be a distance between two locations in a 3-dimensional space, a distance between two locations in a flattened 2-dimensional representation, or some combination thereof.

It will also be understood that while some dimensions are depicted as being along vertical and horizontal directions when viewed as shown in respective figures, a dimension calculated by a system as described herein can include a component along a direction typically associated with the dimension. For example, if a pocket depth of a gum tissue is typically obtained in a conventional mechanical probe generally along the tooth surface defining the pocket, a pocket depth (e.g., d2 in FIGS. 7A to 7C) calculated by a system as described herein can also be a distance measured generally along the tooth surface.

It is also noted that in some example, a feature such as 112 of a bone structure 14 (e.g., in FIGS. 6A and 6C) is referred to as a top portion. It will be understood that such a top portion is in the context of the tooth 10 and the bone structure 14 being oriented as shown (e.g., for lower set of teeth). Thus, for the purpose of description herein, top portion can refer to an upper edge of a tooth in a lower set of teeth, or a lower edge of a tooth in an upper set of teeth.

The present disclosure describes various features, no single one of which is solely responsible for the benefits described herein. It will be understood that various features described herein may be combined, modified, or omitted, as would be apparent to one of ordinary skill. Other combinations and sub-combinations than those specifically described herein will be apparent to one of ordinary skill, and are intended to form a part of this disclosure. Various methods are described herein in connection with various flowchart steps and/or phases. It will be understood that in many cases, certain steps and/or phases may be combined together such that multiple steps and/or phases shown in the flowcharts can be performed as a single step and/or phase. Also, certain steps and/or phases can be broken into additional sub-components to be performed separately. In some instances, the order of the steps and/or phases can be rearranged and certain steps and/or phases may be omitted entirely. Also, the methods described herein are to be understood to be open-ended, such that additional steps and/or phases to those shown and described herein can also be performed.

Some aspects of the systems and methods described herein can advantageously be implemented using, for example, computer software, hardware, firmware, or any combination of computer software, hardware, and firmware. Computer software can comprise computer executable code stored in a computer readable medium (e.g., non-transitory computer readable medium) that, when executed, performs the functions described herein. In some embodiments, computer-executable code is executed by one or more general purpose computer processors. A skilled artisan will appreciate, in light of this disclosure, that any feature or function that can be implemented using software to be executed on a general purpose computer can also be implemented using a different combination of hardware, software, or firmware. For example, such a module can be implemented completely in hardware using a combination of integrated circuits. Alternatively or additionally, such a feature or function can be implemented completely or partially using specialized computers designed to perform the particular functions described herein rather than by general purpose computers.

Multiple distributed computing devices can be substituted for any one computing device described herein. In such distributed embodiments, the functions of the one computing device are distributed (e.g., over a network) such that some functions are performed on each of the distributed computing devices.

Some embodiments may be described with reference to equations, algorithms, and/or flowchart illustrations. These methods may be implemented using computer program instructions executable on one or more computers. These methods may also be implemented as computer program products either separately, or as a component of an apparatus or system. In this regard, each equation, algorithm, block, or step of a flowchart, and combinations thereof, may be implemented by hardware, firmware, and/or software including one or more computer program instructions embodied in computer-readable program code logic. As will be appreciated, any such computer program instructions may be loaded onto one or more computers, including without limitation a general purpose computer or special purpose computer, or other programmable processing apparatus to produce a machine, such that the computer program instructions which execute on the computer(s) or other programmable processing device(s) implement the functions specified in the equations, algorithms, and/or flowcharts. It will also be understood that each equation, algorithm, and/or block in flowchart illustrations, and combinations thereof, may be implemented by special purpose hardware-based computer systems which perform the specified functions or steps, or combinations of special purpose hardware and computer-readable program code logic means.

Furthermore, computer program instructions, such as embodied in computer-readable program code logic, may also be stored in a computer readable memory (e.g., a non-transitory computer readable medium) that can direct one or more computers or other programmable processing devices to function in a particular manner, such that the instructions stored in the computer-readable memory implement the function(s) specified in the block(s) of the flowchart(s). The computer program instructions may also be loaded onto one or more computers or other programmable computing devices to cause a series of operational steps to be performed on the one or more computers or other programmable computing devices to produce a computer-implemented process such that the instructions which execute on the computer or other programmable processing apparatus provide steps for implementing the functions specified in the equation(s), algorithm(s), and/or block(s) of the flowchart(s).

Some or all of the methods and tasks described herein may be performed and fully automated by a computer system. The computer system may, in some cases, include multiple distinct computers or computing devices (e.g., physical servers, workstations, storage arrays, etc.) that communicate and interoperate over a network to perform the described functions. Each such computing device typically includes a processor (or multiple processors) that executes program instructions or modules stored in a memory or other non-transitory computer-readable storage medium or device. The various functions disclosed herein may be embodied in such program instructions, although some or all of the disclosed functions may alternatively be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." The word "coupled", as generally used herein, refers to two or more elements that may be either directly connected, or connected by way of one or more intermediate elements. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or" in reference to a list of two or more items, that word covers all of the following interpretations of the word: any of the items in the list, all of the items in the list, and any combination of the items in the list. The word "exemplary" is used exclusively herein to mean "serving as an example, instance, or illustration." Any implementation described herein as "exemplary" is not necessarily to be construed as preferred or advantageous over other implementations.

The disclosure is not intended to be limited to the implementations shown herein. Various modifications to the implementations described in this disclosure may be readily apparent to those skilled in the art, and the generic principles defined herein may be applied to other implementations without departing from the spirit or scope of this disclosure. The teachings of the invention provided herein can be applied to other methods and systems, and are not limited to the methods and systems described above, and elements and acts of the various embodiments described above can be combined to provide further embodiments. Accordingly, the novel methods and systems described herein may be embodied in a variety of other forms; furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure.

The invention claimed is:

1. A method for measuring a periodontal condition, the method comprising:

generating or obtaining radiograph data for a tooth and a respective bone structure;

generating or obtaining surface data for the tooth, the surface data including surface information of a gum tissue associated with the tooth;

combining the radiograph data and the surface data to generate combined data, such that a feature of the tooth in the radiograph data matches with a corresponding feature of the tooth in the surface data; and calculating a dimension from the combined data, the dimension indicative of the periodontal condition, the calculating of the dimension including generating a merged data plane that extends through the tooth and includes a gumline location on a selected side of the tooth such that the merged data plane forms an angle with respect to a tangent line at the gumline location, the angle having a value in a range of 60 degrees to 120 degrees, 70 degrees to 110 degrees, 80 degrees to 100 degrees, or 85 degrees to 95 degrees.

2. The method of claim 1, wherein the radiograph data includes computed tomography (CT) radiograph data.

3. The method of claim 2, wherein the CT radiograph data includes cone beam computed tomography (CBCT) radiograph data.

4. The method of claim 1, wherein the surface data includes scan data.

5. The method of claim 4, wherein the scan data includes intraoral scan data.

6. The method of claim 1, wherein the calculating of the dimension further includes determining a distance between the gumline location and a bone location.

7. The method of claim 6, wherein the determining of the distance includes identifying the gumline location and the bone location.

8. The method of claim 7, wherein each of either or both of the gumline location and the bone location is identified with one or more algorithms having some or all of artificial intelligence, machine learning and neural network functionalities.

9. The method of claim 7, wherein the gumline location is identified based on an intersection of a first segment representative of the matched feature of the tooth and a second segment representative of a feature of the gum tissue.

10. The method of claim 9, wherein the second segment extends away from the tooth at an angle.

11. The method of claim 9, wherein the bone location is calculated based on an intersection of a third segment representative of a feature of the tooth and a fourth segment representative of a feature of the bone structure.

12. The method of claim 11, wherein the fourth segment extends away from the tooth at an angle.

13. The method of claim 6, wherein the calculating of the dimension further includes subtracting a value from the distance between the gumline location and the bone location.

14. The method of claim 13, wherein the value includes a biologic width value.

15. The method of claim 1, further comprising calculating a second dimension from the combined data to obtain additional information about the periodontal condition.

16. The method of claim 15, wherein the second dimension includes a gum pocket depth dimension, a gum recession dimension or a clinical attachment level dimension.

17. A system for measuring a periodontal condition, the system configured to generate combined data including a combination of radiograph data for a tooth and a respective bone structure and surface data for the tooth and a respective gum tissue, the system further configured to calculate a dimension from the combined data, the dimension indicative of the periodontal condition, the calculated dimension based on a merged data plane that extends through the tooth and includes a gumline location on a selected side of the tooth such that the merged data plane forms an angle with respect to a tangent line at the gumline location, the angle having a value in a range of 60 degrees to 120 degrees, 70 degrees to 110 degrees, 80 degrees to 100 degrees, or 85 degrees to 95 degrees.

18. The system of claim 17, wherein the radiograph data includes cone beam computed tomography (CBCT) radiograph data, and the surface data includes intraoral scan data.

19. The system of claim 18, wherein the system includes a CBCT apparatus for generating the CBCT radiograph data, and an intraoral scanner for generating the intraoral scan data.

20. The system of claim 18, wherein at least one of the CBCT radiograph data and the intraoral scan data is obtained from an external source that is not part of the system.

\* \* \* \* \*